United States Patent [19]

Sommergruber et al.

[11] Patent Number: 5,149,783
[45] Date of Patent: Sep. 22, 1992

[54] EXPRESSION OF THE VIRALLY CODED PROTEASE P2A OF HRV2

[75] Inventors: Wolfgang Sommergruber, Vienna; Friederike Fessl, Perchtolsdorf; Ernst Kuechler, Vienna; Dieter Blaas, Vienna; Timothy Skern, Vienna; Manfred Zorn, Vienna; Markus Duechler, Vienna; Heinrich Kowalski, Vienna; Peter Volkmann, Vienna; Ingrid Maurer-Fogy, Vienna, all of Austria; Peter Pallai, Brookfield, Conn.

[73] Assignee: Boehringer Ingelheim International GmbH, Fed. Rep. of Germany

[21] Appl. No.: 288,894

[22] Filed: Dec. 23, 1988

[30] Foreign Application Priority Data

Dec. 23, 1987 [DE] Fed. Rep. of Germany ....... 3743848
Jul. 23, 1988 [DE] Fed. Rep. of Germany ....... 3825118

[51] Int. Cl.$^5$ .......................... A61K 37/02; C12Q 1/70
[52] U.S. Cl. ......................................... 530/326; 435/5; 530/300; 530/826
[58] Field of Search ....................... 530/300, 326, 826; 435/5

[56] References Cited

U.S. PATENT DOCUMENTS 4,652,552 3/1987 Kettner et al. .................. 514/18

FOREIGN PATENT DOCUMENTS

3505148A1 10/1986 Fed. Rep. of Germany .

OTHER PUBLICATIONS

Skern, T. et al., *Nucleic Acids Res.*, 13:2111–2126 (1985).
Duechler, M. et al., *Proc. Natl. Acad. Sci. USA.*, 84:2605–2609 (1987).
Stanway, G. et al., *Nucleic Acids Res.*, 12:7859–7875 (1984).
Callahan, P. et al., *Proc. Natl. Acad. Sci. USA.*, 82:732–736 (1985).
Butterworth, B., *Virology*, 56:439–453 (1973).
McLean and Rueckert, *J. Virol.*, 11:341–344 (1973).
McLean, C. et al., *J. Virol.*, 19:903–914 (1976).
Kowalski, H. et al., *J. Gen. Virol.*, 68:3197–3200 (1987).
Korant, B. et al., *J. Cellular Biochem.*, 32:91–95 (1986).
Geist, F. C. et al., *Antimicrobial Agents Chemotherapy*, 31:622–624 (1987).
Ivanoff, L. A. et al., *Proc. Natl. Acad. Sci. USA.*, 83:5392–5396 (1986).
Toyoda, H. et al., *Cell*, 45:761–770 (1986).
Dewalt, P. et al., *J. Virol.*, 61:2162–2170 (1987).
Werner, G. et al., *J. Virol.*, 57:1084–1093 (1986).
Hanecak, R. et al., *Cell*, 37:1063–1073 (1984).
Korant, B. et al., *Biomed. Biochim. Acta*, 45:1529–1535 (1986).
Klump, W. et al., *Proc. Natl. Acad. Sci. USA.*, 81:3351–3355 (1984).
Nicklin, M. et al., *Proc. Natl. Acad. Sci. USA.*, 84:4002–4006 (1987).
Perrin, D. D. et al., *Int'l Encyc. Pharm. of Therapeut.*, Ses. 111, pp. 288–302 (1984).

*Primary Examiner*—Christine Nucker
*Assistant Examiner*—Laurie Scheiner
*Attorney, Agent, or Firm*—Sterne, Kessler, Goldstein & Fox

[57] ABSTRACT

This invention relates to a DNA molecule or a functional derivative thereof coding for a fusion protein, the fusion protein comprising an enzymatically active component and a non-enzymatically active polypeptide component which may be cleaved therefrom, an expression system which contains the DNA molecule, the use thereof as a test system for inhibitors of viral proteases, and an assay for identifying viral inhibitors.

1 Claim, 17 Drawing Sheets

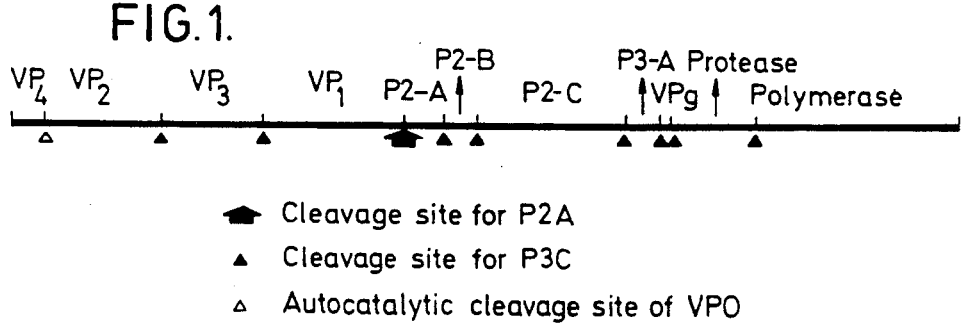

FIG. 1.

- Cleavage site for P2A
- Cleavage site for P3C
- Autocatalytic cleavage site of VPO

FIG. 2.

Cleavage Sites

| Protein Junction | HRV89 | HRV2 | HRV14 | PV1 |
|---|---|---|---|---|
| VP4/VP2 | LQ SP | LQ SP | LN SP | LN SP |
| VP2/VP3 | TQ GL | RQ GL | PQ GL | LQ GL |
| VP3/VP1 | TQ NP | AQ NP | TE GL | AQ GL |
| VP1/P2A | NV GP ? | TA GP | SY GL | TY GE |
| P2A/P2B | EQ GL | EQ GV | EQ GL | GQ GI |
| P2B/P2C | KQ SD | KE SD | RQ AN | KQ GD |
| P2C/P3A | FQ GI | FQ GP | FQ GP | FQ GP |
| P3A/VPg | LQ GP | LQ GP | TQ GP | HQ GA |
| VP Protease | TQ GP | TQ GP | VQ GP | VQ GP |
| Protease/Polymerase | TQ GL | VQ GQ | KQ GQ | SQ GE |

FIG. 8.

Catalytic region — P2A

```
              ↓               ↓
HRV2:   P G D C G G K L L C K H G V
HRV89:  P G D C G G K L L C K H G V
HRV14:  P G D C G G I L A C I H G P
PV1:    P G D C G G I L A C H H G V
```

Catalytic region — P3C

```
              ↓                       ↓
HRV2:   T K S G Y C G G V L Y K I G Q V L G I H V G G N G R
HRV89:  T K A G Y C G G V V Y K V G Q V L G I H V G G N G R
HRV14:  T K T G Q C G G V L C A T G K I F G I H V G G N G R
PV1:    T R A G Q C G G V I T C T G L S S G C M L V D G S H
```

FIG. 9.

```
I  M  T  R  I  Y  H  K  A  K  H  V  K  A  W  C  P  R  P  P  R  A  L  E  Y  T  R  A  H  R  T  N  F
TATAATGAGACAAGAATCTATCACACAAGGCTAAACATGTCCAAGGCATGCCCACCAGAGCGCTTGAGTATACTCGTCGCTCATCGCACTAATTTT
        3010       3020       3030       3040       3050       3060       3070       3080       3090       3100
                                                            VP1→
                                                             G  P  S  D  M  Y  V  H  V  G  N  L  I
 K  I  E  D  R  S  I  Q  T  A  I  V  T  R  P  I  I  T  T  A
AAAATTGAGGATAGGAGTATTCAGACAGCAATTGTGACCAGACCAATTATCACTACAGCTGGCCCAGTGACATGTATGTTCATGTAGGTAACCTTATTT
        3110       3120       3130       3140       3150       3160       3170       3180       3190       3200

Y  R  N  L  H  L  F  N  S  E  M  H  E  S  I  L  V  S  Y  S  S  D  L  I  I  Y  R  T  N  T  V  G  D  D
ATAGAAATCTTCATCTTTTCAACTCTGAGATGCATGAATCTATTTTGGTATCTTATTCATCAGATTTAATCATTTACCGAACAAACACTGTAGGTGATGA
        3210       3220       3230       3240       3250       3260       3270       3280       3290       3300

Y  I  P  S  C  D  C  T  Q  A  T  Y  Y  C  K  H  K  N  R  Y  F  P  I  T  V  T  S  H  D  W  Y  E  I
TTACATTCCCTCTTGTGATTGTACCCAAGCTACTTATTATTGCAAAATATAGATACTCCCAATTACAGTACAAGCCATGACTGGTATGAAATA
        3310       3320       3330       3340       3350       3360       3370       3380       3390       3400
                              P2A

Q  E  S  E  Y  Y  P  K  H  I  Q  Y  N  L  L  I  G  E  G  P  C  E  P  G  D  C  G  G  K  L  L  C  K
CAGGAAAGTGAGTACTATCCCAAACATATACAGTACAATTTGTTGATTGGTGAAGGCCCTTGTGAACCAGGTGACTGTGGTGGAAAAGTTGCTATGCAAAC
        3410       3420       3430       3440       3450       3460       3470       3480       3490       3500
                              P2B

H  G  V  I  G  I  V  T  A  G  G  D  N  H  V  A  F  I  D  L  R  H  F  H  C  A  E  E  Q  G  V  T  D  Y
ATGGTGTCATAGGTATAGTAACAGCTGGTGGTGATAATCATGTGGCTTTTATTGACCTTAGACACTTCCATTGTGCTGAAGAACAAGGGGTTACAGATTA
        3510       3520       3530       3540       3550       3560       3570       3580       3590       3600

I  H  M  L  G  E  A  F  G  N  G  F  V  D  S  V  K  E  H  I  H  A  I  N  P  V  G  N  I  S  K  K  I
TATACATATGCTAGGAGAAGCATTTGGAAATGGATTTGTAGATAGTGTAAAAGAACATATACATGCCATAAACCCAGTAGGAAATATCAGCAAGAAAATT
        3610       3620       3630       3640       3650       3660       3670       3680       3690       3700
```

FIG. 14
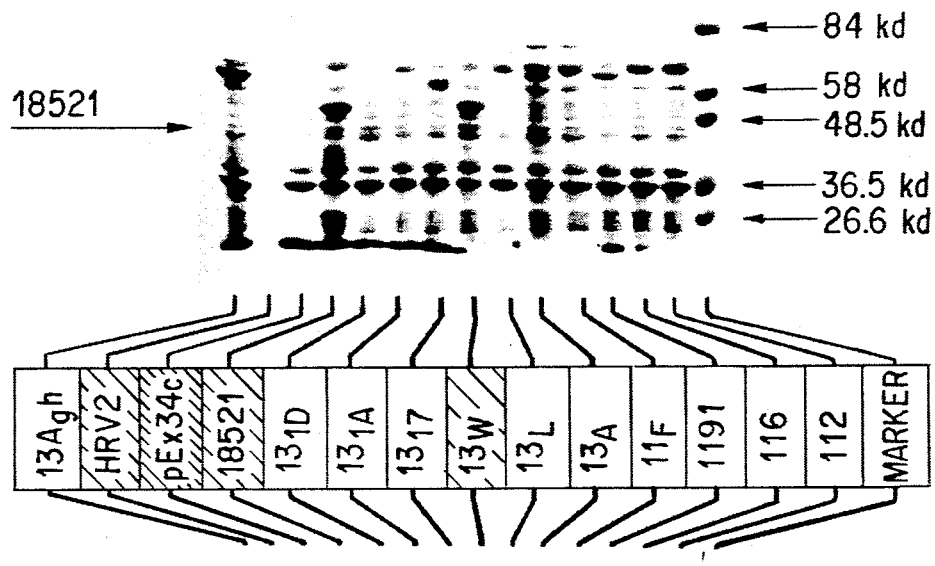
FIG. 16
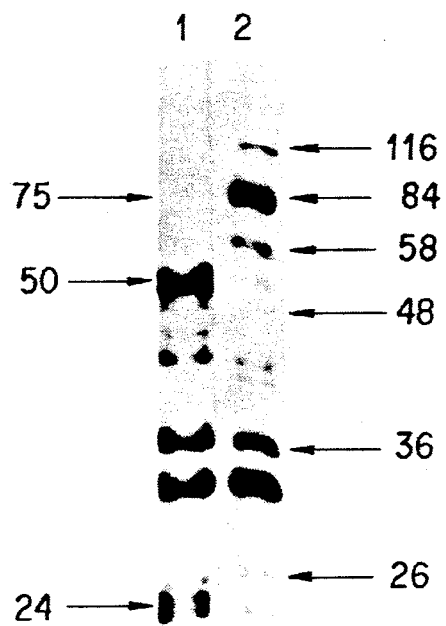

HRV2 protease 2A

```
                                              ┌─→ 2A cleavage site
-----------VP1----------------→│
n f k i e d r s i q t a i v t r p i i t t a G p s d m y v h v g n l i
                                           ▼ 1                    10
                                           y y r N I H I f n s e m h e s i l v s y s s D L I l y r t n t v G
      20                    30                    40 d d y l p s C d C t q a t Y y c k h k n r y f P l t v t s h d w
      50              60                    70 y e l q e s e Y Y P k h l Q y n l l l g e G p c e  P G D C G G k
      80              90                  100      ▲ ▲ ▲ ▲ ▲ ▲
                                                   G △ S △ △

```
Chymotrypsin      GASGVSSCMGDSGGPLVCKKNGAWTLVGIVSWGSSTCSTSTPGVYARVTA
P2A / HRV2        LLIGEGPCEPGDCGGKLLCKHGVIGIVTAGGDNHVAFIDLRHFHCAEEQ
P2A / Polio       MLIGHGFASPGDCGGILRCHHGVIGIITAGGEGLVAFTDIRDLYAYEEEA
Trypsin           LEGCKDSCQGDSGGPVVCNGQLQGIVSWGYGCAQKNKPGVYTKVCNYVNW
Compl. Fact. D    SNRRDSCKGDSGGPLVCGGVLEGVVTSGSRVCGNRKKPGIYTRVATYAAW
Protease B        GMIRTNVCAEPGDSGGPLYSGTRAIGLTSGGSGNCSSGGTTFFQPVTEAL
Kallikrein        GGKDACKGDSGGPLVCKHNGMWRLVGITSWGEGCARREQPGVYTKVAEYM
Trypsinlike P.    AASGKDACQGDSGGPLVSGGVLVGVVSWGYGCAYSNYPGVYADVAVLRSW
EGF binding P.    MGGGKDTCAGDSGGPLICGGILQGITTSNGPEPCGKPGVPAIYTNLIKFNS
Tonin             EGGKDTCAGDSGGPLICDGVLQGITSGGATPCAKPKTPAIYAKLIKFTSW
Nerve Growth F.   MDGGSYTCEHDSGGPLICDGILQGITSWGPEPCGEPTEPSVYTKLIKFSS
Thaumatin I       DDSGSGICKTGDCGGLRCKRFGRPPTTLAEFSLNQYGKDYIDISNIKGF
```

EXPRESSION OF THE VIRALLY CODED PROTEASE P2A OF HRV2

BACKGROUND OF THE INVENTION

1. Field of the Invention

The present invention relates to DNA molecules which code for fusion proteins from enzymatically active fractions and polypeptide fractions which can be cleaved therefrom, expression systems which contain these DNA molecules and the use thereof as test systems for inhibitors of viral proteases.

2. Description of the Background Art

Rhinoviruses are ss(+)RNA viruses and represent a genus within the Picornaviridae (Cooper, P.D. et al., *Intervirology* 1:165-180; (1978); MacNaughton, M. R., *Current Top. Microbiol. Immunol.* 97:1-26 (1982)). They are widespread, attack the upper respiratory tract in humans and result in acute infections which lead to colds, coughs, sore throat, etc. and are generally referred to as colds (Stott, E. J. et al., *Ann Rev. Microbiol.* 26:503-524 (1972)). Infections caused by rhinoviruses are among the commonest diseases in man. Admittedly, the illness is usually harmless but because of the temporary weakening of the body, secondary infections caused by other viruses or bacteria occur, which may under certain circumstances, result in serious illness. Of the total of about 115 different know serotypes of human rhinoviruses, until now, 3 serotypes have been closed and completely sequenced: German Patent Application P 35 05 148.5; Skern; T. et al., *Nucleic Acids Res.* 13:2111-2126 (1985); Duchler, M. et al., *Proc. Natl. Acad. Sci. U.S.A.* 84:2605-2609 (1987); Stanway, G. et al., *Nucleic Acids Res.* 12:7859-7877 (1984); Callahan, P. L. et al., *Proc. Natl. Acad. Sci. U.S.A.* 82:732-736 (1985)).

Comparison of the amino acid sequences of the individual proteins shows that the viral enzymes are particularly well preserved. Thus, the homology between the protease P2A of HRV89 and HRV2 is about 85%; in protease P3C, 75% of the amino acids are identical (Duchler, M. et al., (1987)). These levels are substantially above the average percentages observed in the protein as a whole. It can, therefore, be assumed that it is precisely the viral enzymes which are particularly well preserved in evolution and are very similar in their properties in different rhinoviruses.

Hardly any other viral system is so dependent in its regulation of the course of infection, on a controlled limited proteolysis as that of the picornaviridae. The genomic single-stranded (+)RNA of the rhinoviruses is modified shortly after infection by the cleaving of the oligopeptides VPg bound to the 5' end which serves as mRNA for the synthesis of a polyprotein which includes the entire continuous reading frame of the nucleic acid sequence (Butterworth, B. E., *Virology* 56:439-453 (1973); McLean, C. et al., *J. Virol.* 11:341-344 (1973); McLean, C. et al., *J. Virol,* 19:903-914 (1976)). The mature viral proteins are formed exclusively by proteolytic cleaving from this polyprotein, the effective proteases themselves being part of this polyprotein. The first step in this processing is the cleaving of the precursor stage of the coat proteins which is effected by the protease P2A. In the succession of the genes, the sequence of the protease P2A is immediately after the fragment coding for the coat protein. P2A is, therefore, the first detectable enzymatic function of the virus because of its location in the polyprotein.

To some extent, P2A cleaves automatically from the precursor of the coat proteins and is responsible for the separation of the capsid precursor P1 from the rest of the polyprotein. Separation of the coat protein region from the fragment responsible for replication is already taking place during translation of the polyprotein.

This step is essential for the further progress of the viral infection. It is known of the polio virus system that, in all probability, all the enzymes involved in this maturation cleaving are virally coded (Toyoda, H. et al., *Cell* 45:761-770 (1986)). In the polio virus, there are three types of cleaving signals (FIG. 1); the Q-G site which is used most and which is recognized by the viral protease P3C, and the Y-G site which is used by P2A as a recognition signal. Initially, the protease P3C was of central interest in explaining the proteolytic processing of picorna viruses. Very early on, it was possible to describe a proteolytic activity equivalent to P3C in EMC (Pelham, H. R. B., *J. Biochem.* 85:457-461 (1978); Palmenberg, A. C. et al., *J. Virol,* 32:770-778 (1979)). In the course of further investigations, it was found that the leader peptide (L) of cardio viruses (e.g., EMCV) and aphto viruses (e.g., FMDV) which is not present in rhino- and entero viruses, is involved in proteolytic processing of EMCV (Palmenberg, A. C., *J. Cell, Biochem.* 331191-1198 (1987)). It was subsequently possible to demonstrate, by isolating polio P3C and using immunological methods, that P3C autocatalytically cuts itself out of the polyprotein in order to attack all potential Q-G cleaving sites in "trans".

The use of recombinant systems which represented, inter alia, the P3C region, made it possible to express the P3C of some entero- and rhino viruses (Werner, G. et al., *J. Virol,* 57:1084-1093 (1986)) and accurately to characterize the P3C of polio (Hanecak, R. et al., *Cell* 37:1037-1073 (1984); Korant, B. D. et al., *Biomed. Biochim. Acta* 45:1529-1535 (1989)) and the equivalent proteolytic function in FMDV (Klump, W. et al, *Proc. Natl, Acad. Sci. U.S.A.* 81:3351-3355 (1984); Burroughs, J. N. et al., *J. Virol.* 50:878-883 (1984)). By mutagenesis studies in vitro, it was possible to demonstrate that the replacement of the highly preserved amino acids cysteine (position number 147) and histidine (position number 161) in P3C of polio virus leads to an inactive enzyme, whereas the mutation of htenon-conversed cysteine (position number 153) has no appreciable effect on the proteolytic activity of polio P3C. It was further concluded that polio P3C belongs to the cysteine proteases (Ivanoff, L. A. et al., *Proc. Natl. Acad. Sci. U.S.A.* 83:5392-5396 (1986)). It was also possible to show, by in vitro mutagenesis of polio P3C (i.e., by replacement of the preserved valine by alanine in position 54 of the protease) that this mutation in a full size cDNA of polio after transfection into COS1 cells results in a polymerase-deficient virus (Dewalt, P. G. et al., *J. Virol.* 61:2162-2170 (1987)).

Antibodies developed against poliko P3C did admittedly prevent any cleaving carried out at Q-G, but did not prevent cleaving between Y-G (Hanecak, R. et al., *Proc. Natl., Acad. Sci. U.S.A.* 79:3973-3977 (1982)). This observation lead to the conclusion that proteolytic processing at Y-G sites requires its own protease. The seat of this second proteolytic activity was clearly identified as being in P2A within the polio virus. It was interesting to discover that P2A carries out alternative cleaving in the protease-polymerase region (3CD) which also takes place at a Y-G site. However, this cleaving would appear not to have any biological significance curing replication of the virus (Toyoda, H. et al. loc. cit.). Since the synthesis of the host protein is very rapidly stopped during infection with polio virus in Hela cells, but the translation of the polio virus RNA can proceed unimpeded, it was assumed that one or more regulating factors of the translation were altered during the infection. In fact, earlier findings show that the eukaryotic initiation factor 4F is changed by proteolytic cleaving of the p220 component during polio virus infection in Hela cells (Etchison, D. et al., *J. Virol.* 51:832-837 (1984); Etchison, D. et al., *J. Biol. Chem.* 257:14806-14810 (1982)). Subsequently, it was shown that P2A is indirectly responsible for this modification of p220 in infected cells (Krausslich, H. G. et al., *J. Virol.* 61:2711-2718 (1987). The question as to the transactivity of the two proteases P3C and P2A could thus be answered in the affirmitive in the polio virus system insofar as polio viruspolypeptide precursors expressed in vitro which contained the proteolytic recognition sequences were able to be processed by exogenous P3C or P2A proteases (Nicklin, M. J. H. et al., *Proc. Natl. Acad. Sci. U.S.A.* 84:4002-4006 (1987)).

It was also very interesting to discover that two proteins similar to the picornaviral proteases P3C and P2A were discovered in the plant viral system of Comoviridae (Cowpea Mosaic Virus) (Garcia, J. A. et al., *Virology* 159:67-75 (1987); Verver, J. et al., *EMBO* 6:549-554 (1987)). These two viral proteins are involved in the proteolytic processing of the two polyproteins coded by two separately packed ss (+)RNA molecules (B and M RNA), the two Cowpea mosaic virus proteases showing great similarity to the picorna viruses in sequence and cleaving specificity. This remarkable homology of non-structural proteins between Picorna and Comoviruses not only indicates a genetic relationship between these two families of virus but also shows how essential viral proteolytic processing is for these two families of viruses.

The third type of viral maturation cleaving, namely that of VPO (precursor protein of VP2 and VP4), has been described, in the case of Mengo and Rhino virus, with the aid of X-ray structural data. This latter proteolytic event in viral maturation appears to be based on an unusual autocatalytic serine protease type in which basic groups of the viral RNA participate in the formation of the catalytic center, these basic groups acting as proton acceptors (Arnold, E. et al., *Proc. Natl., Acad. Sci. U.S.A.* 84:21-25 (1987)).

The cleavage site specificity of the viral proteases was determined in the polio virus system by N-terminal sequencing of the majority of polio virus proteins (Pallansch, M. A. et al., *J. Virol.* 49:873-880 (1984)). By cloning and sequencing HRV2 (Skern, T. et al., *Nucleic Acids Res.* 13:2111-2126 (1985), it was possible to derive the majority of cleavage sites by sequence comparisons with polio virus and HRV14. Furthermore, the position of the cutting sites between VP4/VP2, VP2/VP3 and BP3/VP1 could be determined by N-terminal sequencing of VP2, VP3 and VP1. The cleavage signal between VP1 and P2A was partly determined by C-terminal sequencing of VP1 (Kowalski, H. et al., *J. Gen. Virol.* 86:3197-3200 (1987). Thus, five different cleavage signals were found in HRV2: Q-S, Q-G, Q-N, A-G and E-S (FIG. 2).

Cysteine proteases are widespread in nature (e.g., papain, cathepsin B, H and S), and their characterization and inhibition is of great scientific and therapeutic value (for a survey see Turk, V., 1986, Cysteine Proteinases and their Inhibitors, Walter de Gruyter; Barrett, A. J. and Salvesen, G., 1986, Proteinase Inhibitors, Elsevier). In the pivorna viral system, too, all kinds of inorganic and organic compounds as well as peptide derivatives and proteins are now known which have an inhibitor effect on the proteolytic processing of these viruses. The effect of these substances is based on the direct interaction with the proteases (Kettner, C. A. et al., U.S. Pat. No.: 4,652,552 (1987); Korant, B. D. et al., *J. Cell. Biochem.* 32:91-95 (1986)) and/or on the indirect route of interaction with substrates of these proteases (Geist, F. C. et al., *Antimicrob. Agents Chemother,* 31:622-624 (1987); Perrin, D. D. et al, Viral Chemotherapy 1:288-189 (1984)). The problem with the majority of these substances is the relatively high concentration needed for inhibition and the in some cases high toxicity of these compounds.

DESCRIPTION OF THE FIGURES

FIG. 1 shows the picorna viral polyprotein and its proteolytic cleavage sites.

FIG. 2 shows cleavage sites in the polyprotein of HRV2, HRV89, HRV14, and polioviruses type 1; those amino acids of HRV2 and 89 which were determined by protein sequencing are underlined.

Trace 1—pAT 153 (control plasmid; $\beta$-lactamase)
Traces 2 and 3—p18731 (deletion mutant of 18521)
Traces 4 and 5—p18521 (expression product with active protease P2A of HRV2)
a = unprocessed fusion protein of 18521 consisting of: MS2-Pol.-VP1-P2A and an N-terminal part of P2B.
b = fusion protein of P18731 shortened by deletion and no longer capable of being processed.
c = processed fusion protein of P18521 consisting of Ms2-Pol. and VP1 (cleavage product is not detectable in p18731).
d = $\beta$-lactamase
e = probably viral protease P2A and an N-terminal part of P2B: formed by autocatalytic cleavage of P18521 (again not present in P18731).

FIG. 8 shows the comparison of amino acid sequence of the probably catalytic region of the viral proteases P2A and P3C of HRV2, 14 and 89 and of polio virus type 1. The amino acids (cysteine and histidine; marked by thick arrows) are probably involved in the structure of the catalytic center.

FIG. 9 shows the nucleotide and amino acid sequence of the viral protease P2A of HRV2. The thick arrows indicate the amino acid position of the two cysteines (106 and 112) and the histidine (in position 114) which may possibly be involved in the structure of the catalytic center.

Figure 10:
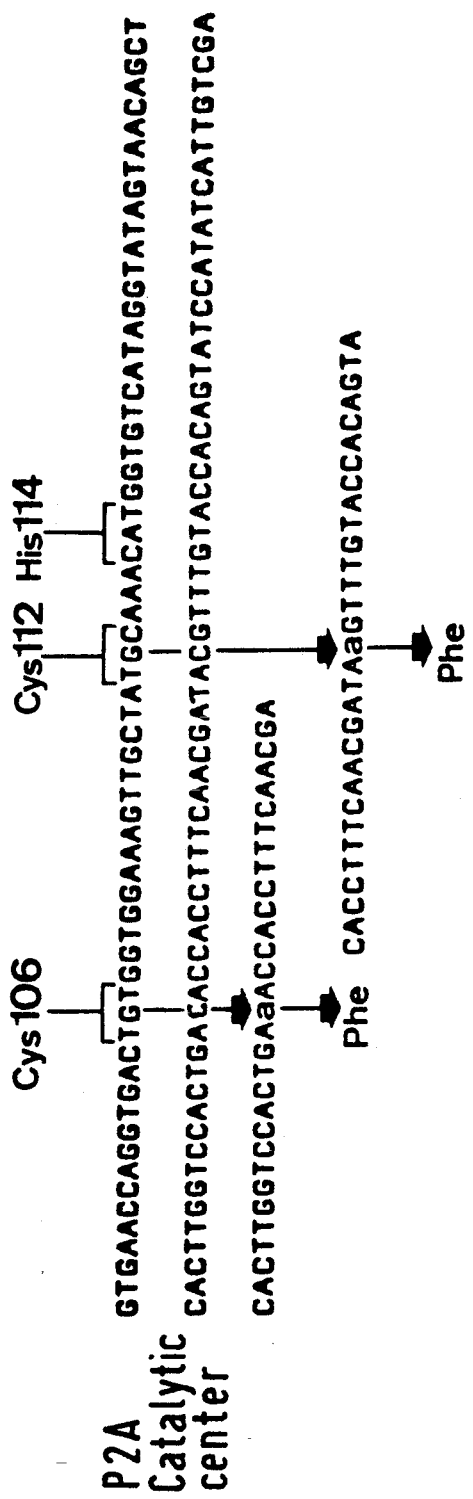

FIG. 10 shows the section of the cDNA of the catalytic center of HRV2-P2A and the sequence of the oligonucleotides for mutagenesis of the two cysteine groups in positions 106 and 112.

Figure 11:
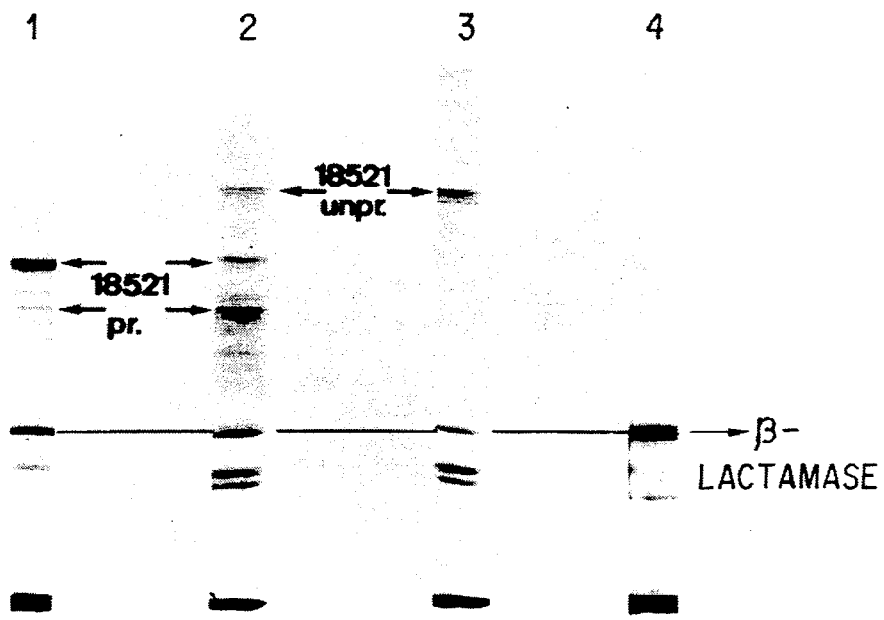

FIG. 11 shows the autoradiogram of the in vitro transcription/translation of the mutated pEx34c×18521:

Trace 1: Replacement of the cysteine in position 112 by phenylalanine in pEx34c×18521.
Trace 2: Non-mutated pEx34c×18521.
Trace 3: Replacement of the cysteine in position 106 by phenylalanine in pEx34c×18521.
Trace 4: pAT153.

Figure 12:
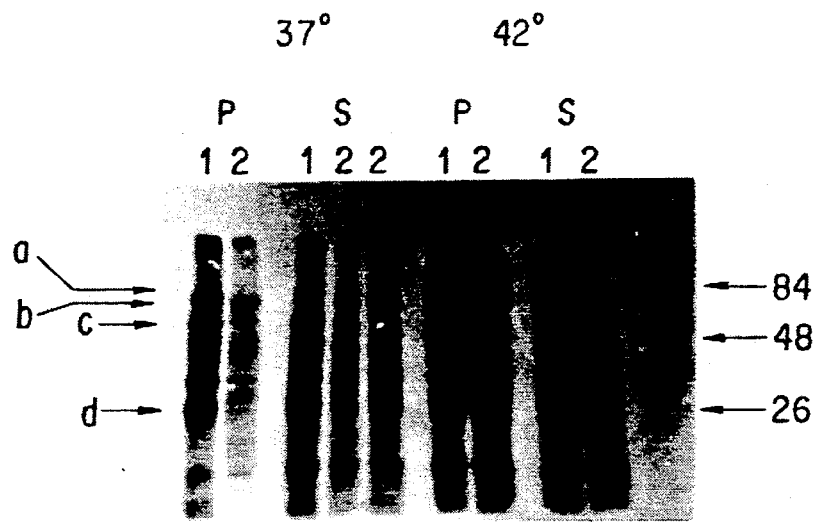

FIG. 12 shows the in vivo labeling of P2A.
1=8521; plasmid with active form of P2A, consisting of: part of the MS2-polymerase/VP1/P2A/N-terminus of P2B (see Example 1).
2=13L; deletion mutant of 18521; HRV2-coding region ends approximately 18 amino acids before the C-terminus of P2A.
P=Pellet
S=Supernatant The temperatures of 37° C. and 42° C. specified are the expression temperatures used in Example 5.
a=Unprocessed expression product of 18521.
b=Unprocessable expression product of 13L.
c=Processed expression product of 18521 consisting of: part of the MS2-polymerase/VP1.
d=Probably P2A representing peptide consisting of P2A/N-terminus of P2B; not present in the non-processing deletion mutant 13L.

Figure 13:
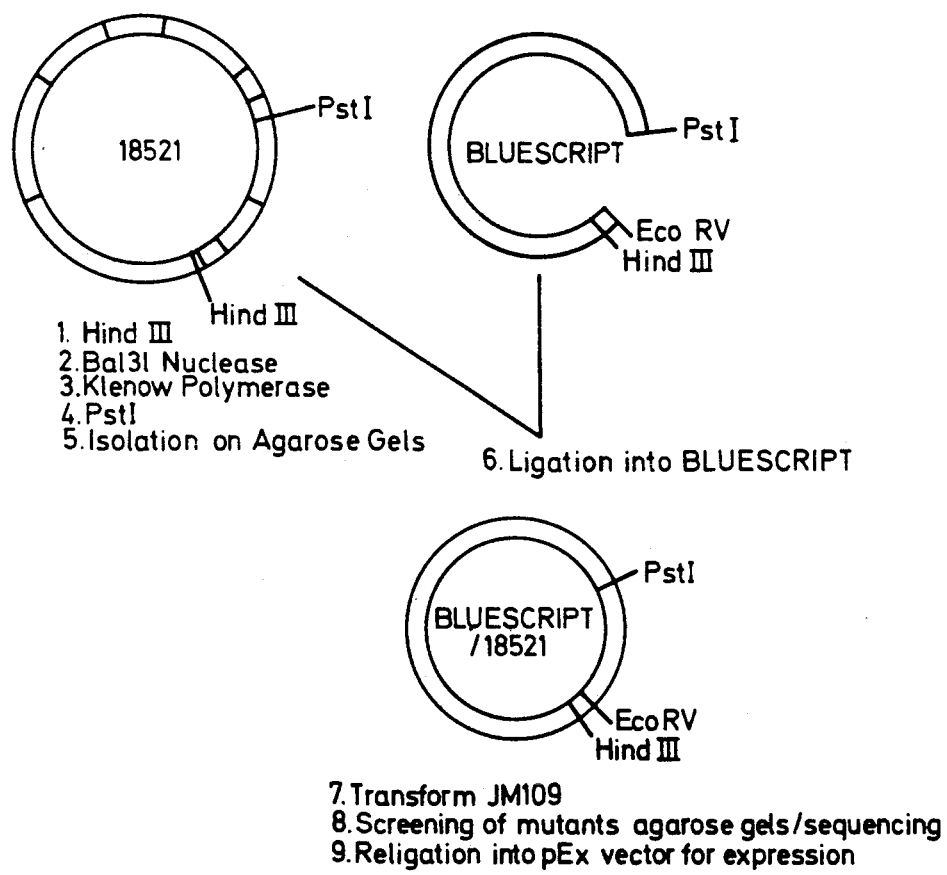

FIG. 13 shows the construction plan for the preparation of deletion mutants of the C-terminal HRV2-P2A-region.

FIG. 14 shows the separation of the expression products of pEx34c×18521 deleted at the C-terminus on a 10% SDS-polyacrylamide gel and staining with Coomassie brilliant blue (top half of the picture), and a Western blot with a polyclonal serum against VP2 of HRV2 (bottom half of the picture). The traces HRV2 (positive control for VP1), pEx34 c (negative control) and 18521 (positive control for proteolytic processing by P2A) serve as reference markers. Apart from 13W, none of the other deletion mutants shows any further proteolytic processing.

FIG. 15 shows the amino acid sequence of HRV2 protease 2A region (in thick lettering). The capital letters indicate the amino acids which are identical between rhino, polio and coxsackie viruses. Double arrows indicate the position and nature of the exchange or deletion used to characterize the probable active center and the C-terminus of the protease 2A of HRV2.

FIG. 16 shows the protein pattern (Coomassie blue) of pEx18521 (trace 1) and the mutant pEx18521[Arg 134—Gln].

Figure 17:
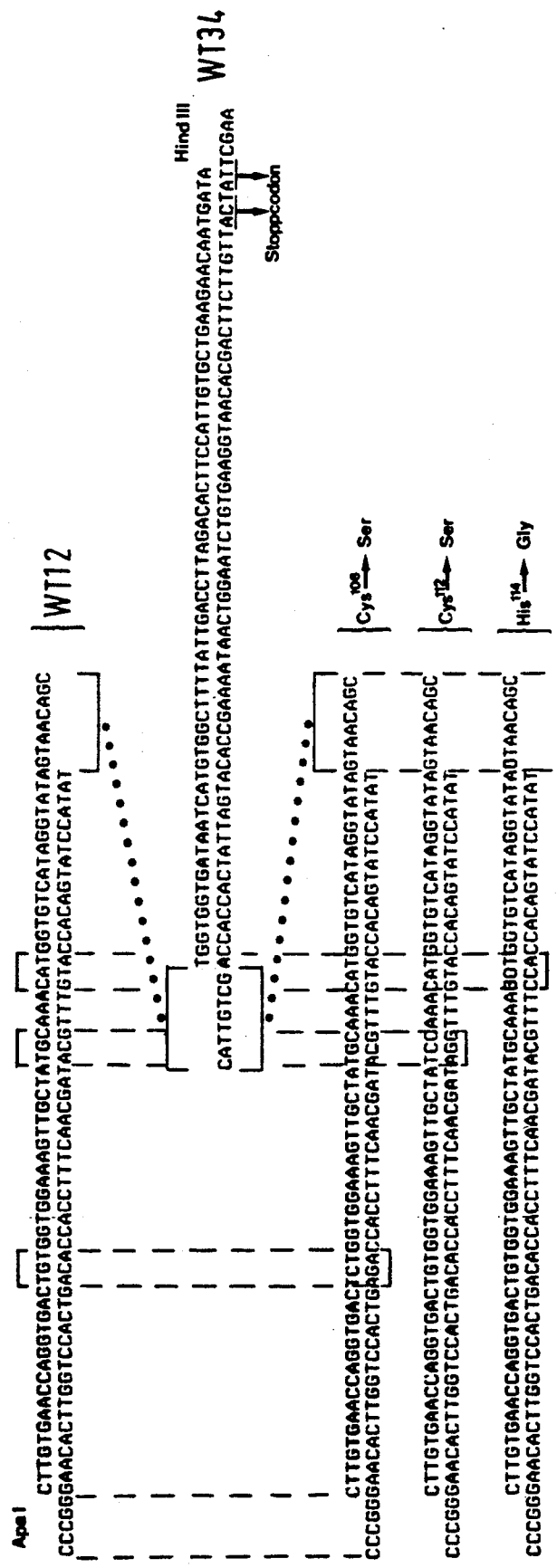

FIG. 17 shows the oligonucleotide cassette for mutagenesis of the probably active center of protease 1A of HRV2. By combining the two double-stranded oligonucleotides WT12+WT34 the coding region for the Wild-type protease 2A is obtained. After the last amino acid of 2A (glutamine 142), two stop codons were introduced. If the double-stranded nucleotide WT34 is combined instead of WT12, with an oligonucleotide which has suitable mutation or deletion because of its altered base sequence, any desired change may be made to the amino acid sequence in this region (here shown by way of example in the construction of the Wild-type-2A and the mutations for Cis 106—Ser, Cis 112—Ser and His 114—Gly).

Figure 18A:
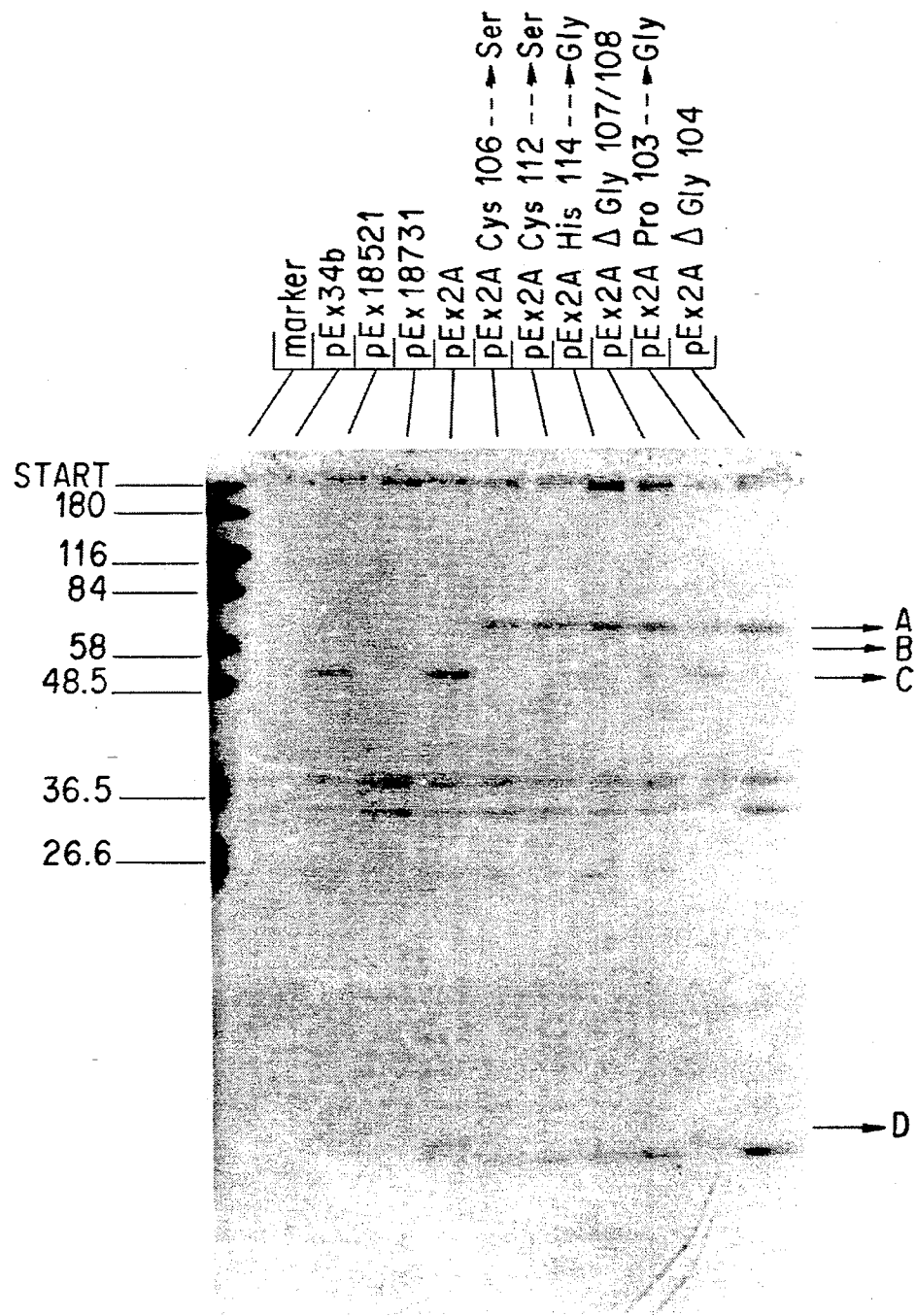

FIG. 18 (a–c) shows the protein pattern of pEx34c (negative control), pEx18521, pEx18731, pEx2a and all the mutants of pEx2A in the probable active center of 2A.

Band A—corresponds to the process expression product (65K) of pEx2A or the mutants of pEx2A.
Band B—corresponds to the expression product (58K) of pEx18731.
Band C—corresponds to the process expression product (50K; MS2-polymerase component+C-terminal part of VP3+entire VP1) of pEx18521, pEx2A and pEx2A [pro103—Gly].
Band D—corresponds to the mature protease 2A (15K).

FIG. 18 (Coomassie blue) shows the protein gel stained with Coomassie blue.

Figure 18B:
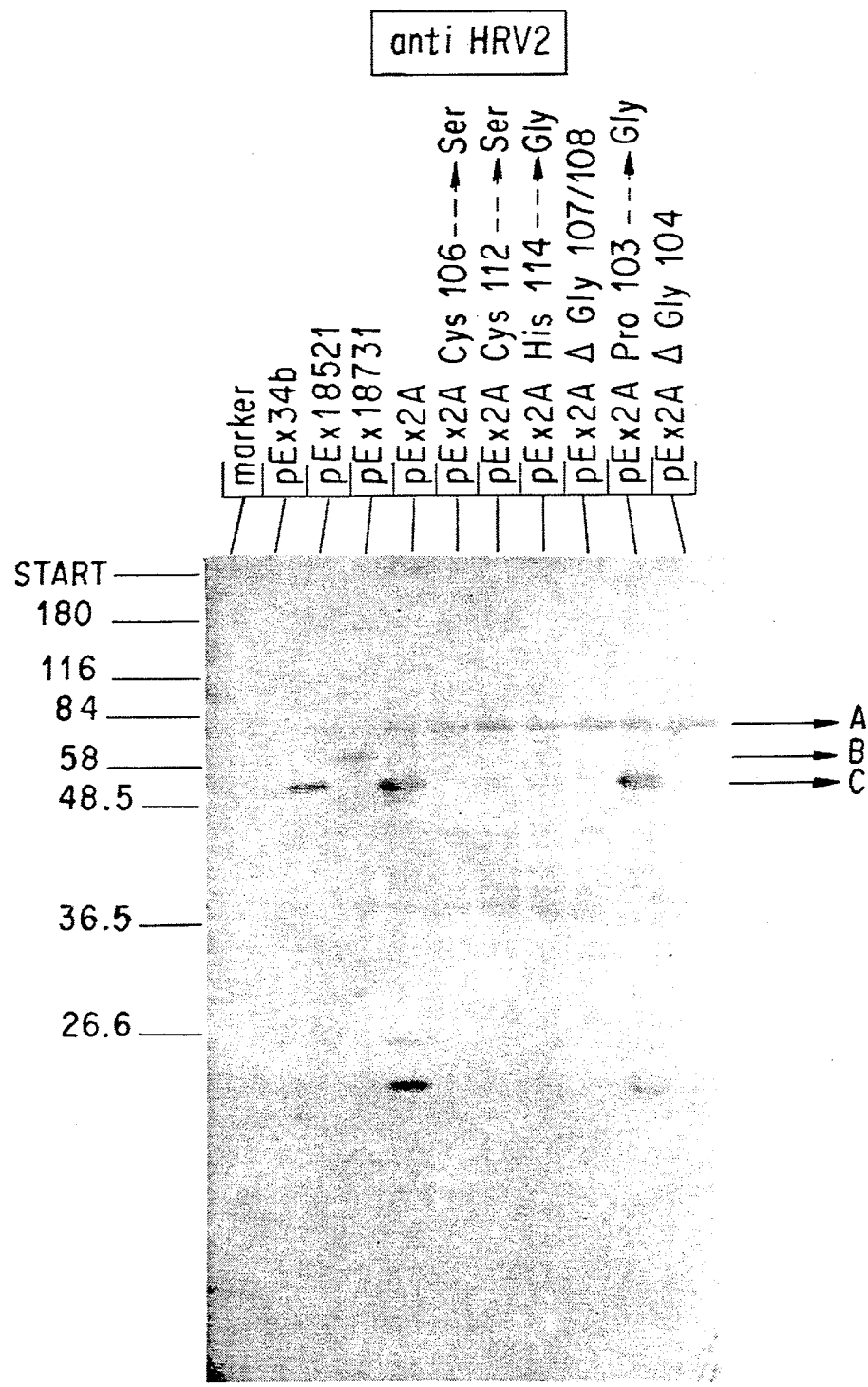

FIG. 18b (Anti-HRV2) shows the western blot of the same gel with a polyclonal antiserum against HRV2.

Figure 18C:
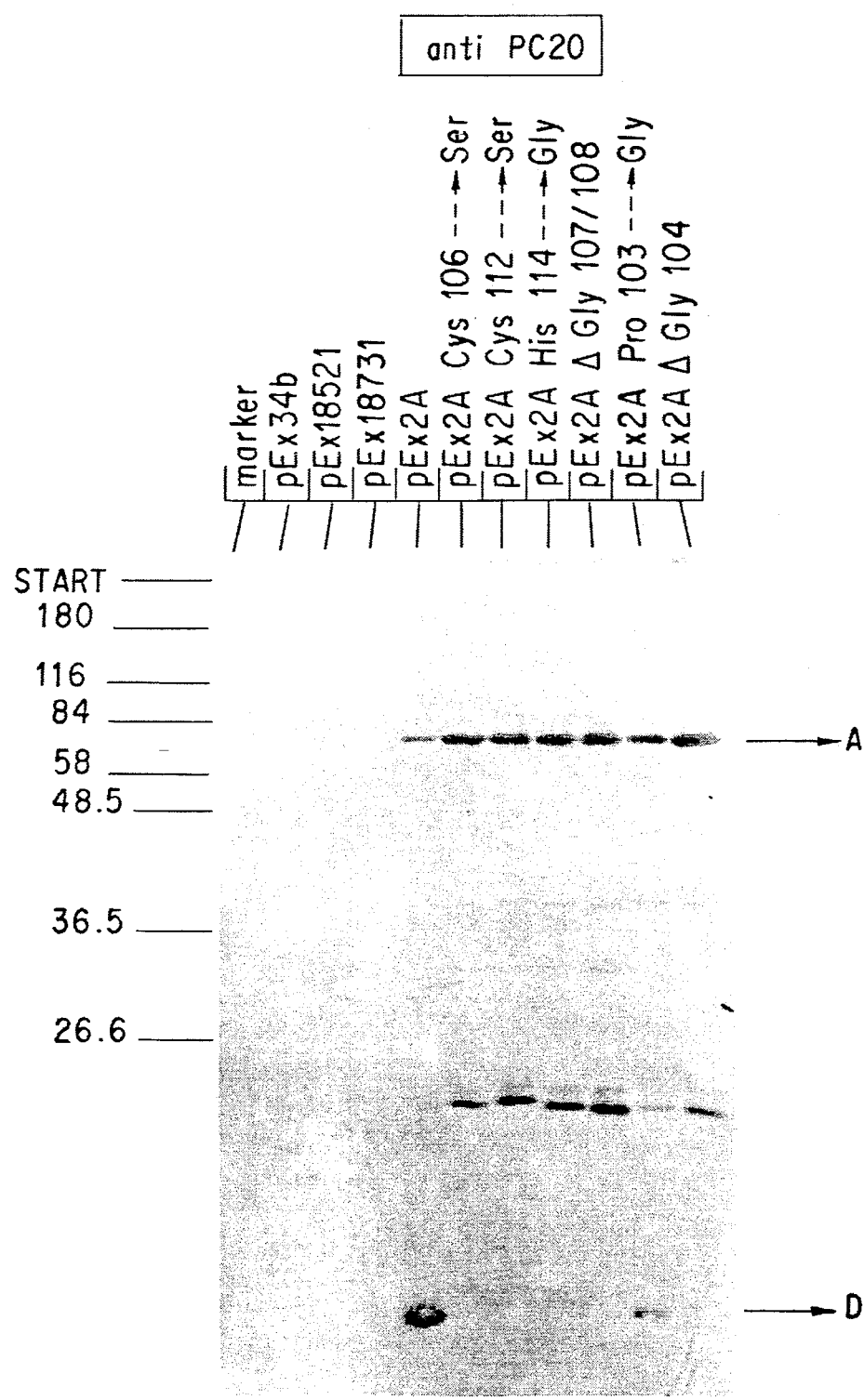

FIG. 18c (Anti-PC20) shows the wester blot of the same gel with a polyclonal antiserum against PC20 (peptide synthesized from the last 20 amino acids of 2A; see Example 7).

Figure 19:
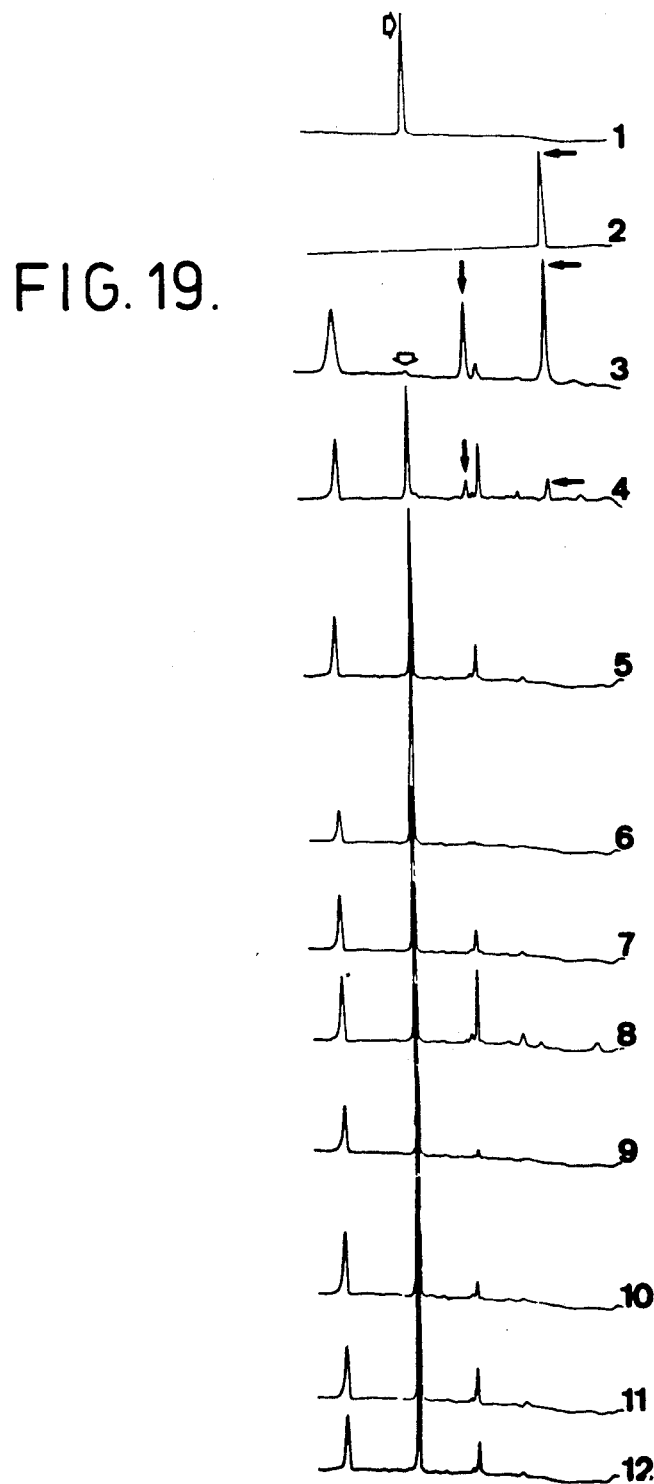

FIG. 19 shows the HPLC profiles of peptides which were isolated after incubation (see Example 9) from supernatants of different 2A expression systems.
1=pure cleavage peptide (Ac-TRPIITTAGPSD-MYVH), $t_R$=12.2 min (fig. horizontal arrow).
2=pure C-terminal cleavage product (GPSDMMYVH), $t_R$=12.2 min (fig. horizontal arrow).
3=peptide pattern when using the pEx2A supernatant, thick vertical arrow shows the second cleavage product (Ac-TRPIITTA), $t_R$=16.8 min.
4=pEx2A[Pro 103—Gly]
5=pEx18521
6 pEx18731
7 pEx2A[Cys 106—Ser]
8 pEx2A[His 114—Gly]
9 pEx2A[Cys 112—Ser]
10 pEx2A[Gly 104]
11 pEx2A[Gly 107/108]
12 pEx34c FIG. 20 shows the comparison of the amino acid sequence of the probable active center of the protease 2A of HRV2 (from amino acid 94 to 142) with the protein sequence databanks PIR and SWISSPORT.

SUMMARY OF THE INVENTION

The present invention relates to a DNA molecule, or a functional derivative thereof, coding for a fusion protein, the fusion protein comprising an enzymatically active component and a non-enzymatically active polypeptide component which may be cleaved therefrom by the enzymatically active component.

The invention further relates to an expression system comprised of a plasmid comprising an insert, wherein the inset is the above-described DNA molecule.

The invention further relates to a method of testing inhibitors of P2A of HRV2 comprising the protein encoded by the above-described DNA molecule with a potential inhibitor and detecting whether the protein encoded by the DNA molecule is cleaved by the P2A after contacting the potential inhibitor.

The invention further relates to an assay for identifying viral inhibitors, the assay comprising the above-described DNA molecule and expression system.

The invention further relates to an antibody which binds to P2A, or a functional derivative thereof.

The invention further relates to a peptide of a formula TRPIITTAGPSDMYVH.

DESCRIPTION OF THE PREFERRED EMBODIMENTS

As shown above, the course of infection by picorna viruses is critically dependent on the viral enzymes. Since precisely these enzymes are particularly well preserved and are very similar in their properties to various rhinoviruses, they suggest themselves immediately as the target for chemotherapy. The viral enzyme P2A is particularly preferred. The chemotherapeutic approach is preferably to inhibit the enzymatic activity by means of, for example, specific inhibitors.

If the first proteolytic activity, the P2A activity, is inhibited, any further maturation process of the viral system is prevented. Because of the marked homology of the P2A region of HRV2 not only with other rhinoviruses but also with representatives of other groups of picorna viridae, it is certainly conceivable that an inhibitor against HRV2-P2A could also be applied to other picorna viruses.

The aim of the present invention is, therefore, to provide a system which it is possible to test potential inhibitors of the viral maturation process.

As used herein, a "functional derivative" of the fusion protein molecule of the invention, is a compound which possesses a biological activity (either functional or structural) that is substantially similar to a biological activity of the molecules of the invention. An example of biological activity is the ability of enzymatically active P2A to cleave the polypeptide component of the fusion protein. A molecule is said to be "substantially similar" to another molecule if both molecules have substantially similar structures or if both molecules possess a similar biological activity. The "functional derivatives" of the invention include both "fragments" and "variants." The term "fragment" is meant to refer to any polypeptide subset of the fusion protein molecule. The term "variant" is meant to refer to a molecule substantially similar in structure to either the entire molecule, or to a fragment thereof provided that the "variant" has at least one biological activity that is similar to an activity of the molecule of the invention. Thus, provided that a molecule possesses at least one biological activity that is similar to an activity of the fusion protein, it is considered a "variant," as that term is used herein, even if one of the molecules contains one or more amino acids not found in the other, or if the sequences of amino acid residues in the two molecules are not identical. Thus, for example, compound lacking (or containing) one or more amino acid residues found (or not found) in the HRV2 fusion protein molecule would be considered to be a variant if that compound possessed a biological activity similar to a biological activity of the HRV2 fusion protein. The term "biological activity" is intended to encompass "catalytic" as well as "structural" activity.

By the term "fusion protein" is meant the protein which is produced when two protein encoding genes are ligated together so that their reading-frames remain in phase.

By the term "enzymatically active" is meant that the enzyme is capable of catalyzing a specific chemical reaction. The preferred enzymatic activity of the present invention is proteolytic activity. The term "proteolytic activity" refers to the braking or cleaving of peptide bonds. A viral protease is an enzyme capable of cleaving a peptide bond.

By the term "viral inhibitor" is meant a compound which prevents viral maturation by preventing the enzymatic activity of a viral protease. The preferred viral protease of the present invention is p2A.

Since P2A is active "in statu nascendi" and is itself part of the substrate, a suitable "substrate enzyme" had to be constructed which would make it possible to monitor the P2A activity by means of its cleavage products. Furthermore, P2A recognizes only one cleavage site in the polyprotein. This very property makes the viral function a suitable target for therapeutic treatment. From this point of view, in the present invention, an expression system for HRV2-P2A was developed for the purpose of characterizing P2A in more detail and establishing a suitable method of discovering inhibitors against P2A.

By the term "expression system" is meant a cloning vehicle designed to promote the expression of a gene insert.

The present invention's expression system, consisting of a plasmid component and an insert, had to be capable of producing a viral polypeptide which would serve as substrate and which would simultaneously also have P2A protease activity. According to the invention, such a system contains as the insert, a DNA molecule which codes for a fusion protein from an enzymatically active component and a non-enzymatically active polypeptide component which can be cleaved therefrom. The enzymatically active component is a viral protease, preferably the viral protease HRV2-P2A. The cleavable polypeptide component is a viral protein, preferably a viral protein VP1, more preferable the viral protein HRV2-VP1, more particularly (VP3)-VP1 of HRV2 or parts thereof.

An example of such a system preferably contains as an insert the HRV2 sequence of 2145-3698 in the correct reading frame. This insert may be introduced into any desired expression vector which is capable of effectively producing the substrate in a suitable host organism transformed with this water. Such an expression vector will preferably contain a ribosomal binding site, a coding region for a fusion component which increases the stability of the expressed fusion protein coded by the insert in the cell, a promoter controlling the fusion protein, a polylinker region in three different reading frames, preferably with cutting sites for restriction enzymes, an "ori" region and a selection marker.

By the term "ribosomal binding site" is meant a particular sequence of nucleotides to which a ribosome will bind.

By the term "coding region" is meant that portion of a gene which directly specifies the amino acid sequence of its protein product.

By the term "promoter" is meant the DNA region, usually upstream to the coding sequence of a gene or operon, which binds RNA polymerase and directs the enzyme to the correct transcriptional start site.

By the term "polylinker" is meant a synthetic oligodeoxyribonucleotide which contains restriction sites.

Polylinkers may be ligated onto the ends of DNA fragments to create restriction sites which may be used in subsequent cloning of the fragment into a vector molecule.

The following expression system is particularly preferred:
- the prokaryotic ribosomal binding site
- part of the coding region for the first 98 N-terminal amino acids of the MS2 polymerase; this fusion component has hydrophobic and basic amino acids and brings about a reduction in the solubility of the fusion protein and increases the stability of the expressed product in the cell.
- the fusion protein is under the control of the left lambda promoter
- a small polylinker region in 3 different reading frames (pExa, b and c) with cutting sites for EcoRI, BamHI, HindIII, PstI, BglII and XbaI makes it possible to insert suitable DNA fragments in phase behind the fusion protein component
- the "ori" and ampicillin-resistance region of pBR322.

Figure 4:
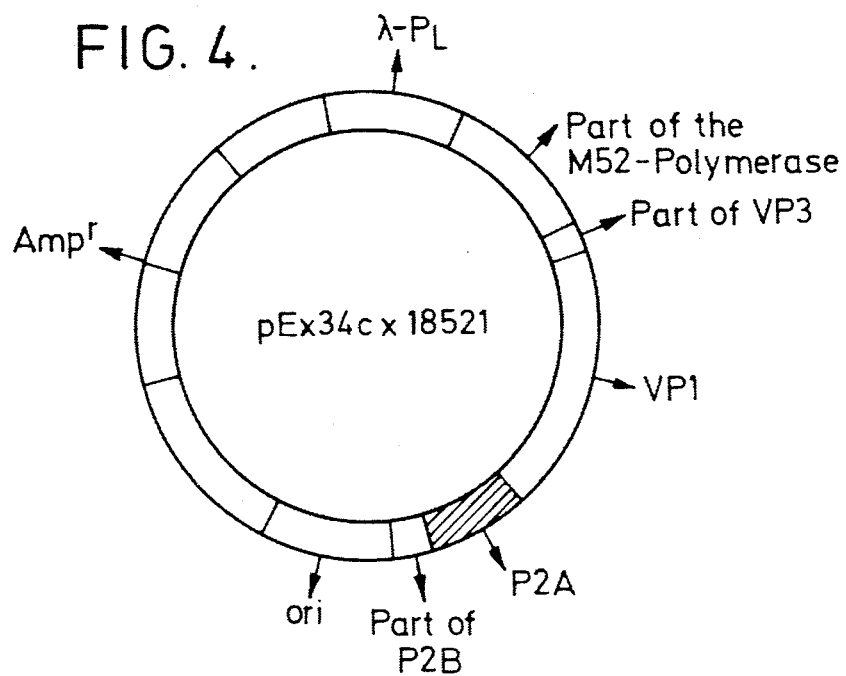
FIG. 4 shows the construction of the expression plasmid pEx34c×18521.

Examples of such vectors are derivatives of the plasmid pPLc-24 (E. Remault et al., *Gene* 15:81–93 (1981)), which were already known as derivatives in the form of pEx vectors from the writings of K. Strebel et al., *J. Virol.* 57:983–991 (1986). The pEx34c expression vector used in the present invention is such a derivative. The abovementioned insert was introduced into this vector as an EcoRI/HindIII fragment. pEx34c×18521 was obtained (FIG. 4). In order to carry our expression studies, an inactive enzyme substrate for P2A was additionally required, which was obtained for example by deletion mutation. A deletion mutant of pEx34c×18521 of this kind was designated pEx34c×18731. This mutant ends at nucleotide number 3321 and therefore no longer possesses the presumed active center of P2A (FIG. 9).

Figure 6:
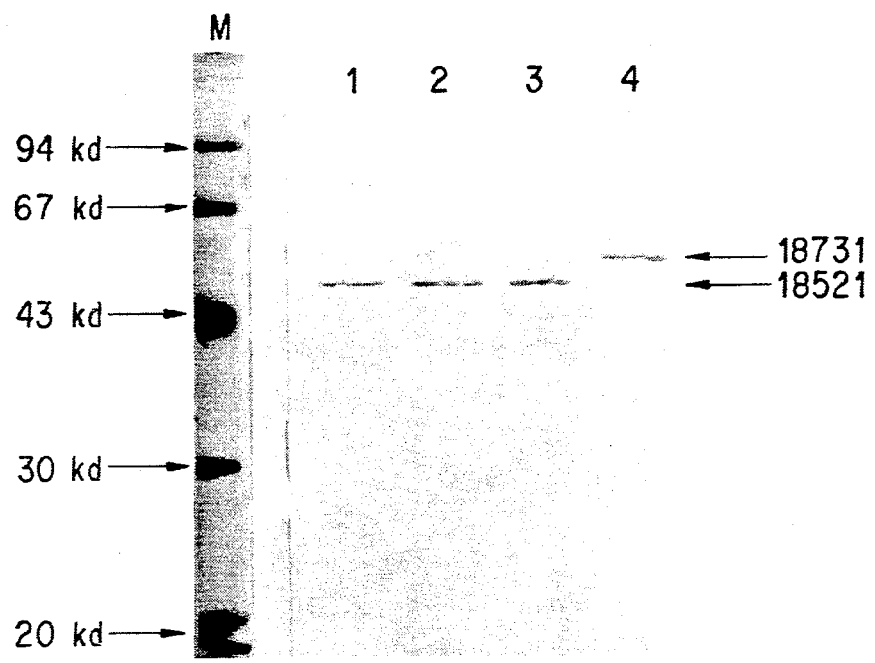
FIG. 6 shows the western blot of the expression products of pEx34c×18521 and 18731 with a polyclonal anti-VP1 serum; in traces 1 to 3, the expression product of three different clones of 18521 has been separated and in trace 4 the expression product of 18731 is separated. The higher molecular bands in traces 1 and 3 which are difficult to see represent the as-yet unprocessed expression product of 18521.

The antigenic specificity of the expressed substrates of pEx34c×18521 and pEx34c×18731 was detected by a Western blot with the aid of a polyclonal serum against VP1 which is an integral component of both plasmids (FIG. 6).

Figure 7:
FIG. 7 shows the autoradiogram of the in vitro transcription and translation of pEx34c×18521 and pEx34c×18731.

To demonstrate the suitability of this system for testing possible inhibitors, the two plasmids were expressed in vitro in a bacterial, cell-free system, such as the "prokaryotic DNA directed translation kit" produced by Amersham. The results are shown in FIG. 7. They indicate that an in vitro system of this kind is exceptionally suitable for testing inhibitors against P2A.

In order to obtain further information as to the catalytic center of the viral protease P2A, mutagenesis studies were carried out on the presumed active center. Since it is supposed to be an SH protease (Cys . . . His in the active center), both the cysteines in question, in positions 106 and 112, were replaced by phenylalanine by oligonucleotide mutagenesis. The plasmids thus mutated were expressed in the prokaryotic in vitro translation system. It was then found that the plasmid in which cysteine at position 112, immediately adjacent to the histidine group, had been replaced, had a higher P2A activity. Mutation at position 106 lead to an inhibition of proteolytic activity.

By in vivo marking of HRV1-P2A and comparison of the expression products of pEx34c×18521 with those of another deletion mutant, essential parts of the C-terminus of P2A could be further secured. This mutant, which ends with the region coding for HRV2 18 amino acids before the carboxy terminus of P2A, was designated 13L (FIG. 14). It was also prepared by the action of the exonuclease Bal31. Both pEx34c—18521 and also 13L were grown in *E. coli* and labelled in vivo with S-35 methionine. The expression products were autoradiographed (FIG. 12). The specific band emanating from the expression system 18521, which represents P2A plus part of P2B, cannot be detected in the expression system of the deletion mutant 13L.

Deletion studies in the C-terminal region of the protease 2A (see Example 5) showed that this region of 2A can be shortened by at least 6 amino acids without affecting the proteolytic processing (see FIG. 14). Deletion between the 10th and 6th amino acid from the C-terminus of 2A (corresponding to the 137th and 133rd amino acids in FIG. 15) obviously results in the destruction of an essential part of 2A. All other mutants which have a deletion of more than 10 amino acids at the C-terminus of 2A also lack the ability to process the VP1/2A cleaving site proteolytically (see Example 5, FIG. 14). There must therefore be essential residues between the 6th and 10th amino acids from the C-terminus which are necessary for the catalytic activity. If one looks at the amino acid sequence of 2A and its amino acids which are highly preserved within the Rhino, Polio and Coxsackie viruses (see FIG. 15), it will be seen that between the 6th and 10th amino acid from the C-terminus of 2A, only the arginine in position 134 is preserved. To find out whether this residue has a fundamental importance in catalysis, arginine 134 was converted into a glutamine by in vitro mutagenesis. As described in Example 2 the mutated expression vector pEx18521[Arg 134—Gln] was expressed and the pattern of the expressed products was analyzed on a protein gel and using a Western blot (see FIG. 16). The significance of Arg 134 could be clearly demonstrated; the mutation of arginine 134 into glutamine results in the disappearance of the proteolytic activity; the unprocessed 75K protein is exclusively formed.

By comparing the amino acid sequence of the proteases 2A and 3C of Rhino, Polio and coxsackie viruses and by in vitro mutagenesis studies on protease 3C of polio (Ivanoff, L. A. et al., *Proc. Natl. Acad. Sci. U.S.A.* 83:5392–5396 (1986)) it can be assumed that these enzymes use a cysteine and histidine in the active center for proteolysis. In the case of the protease 2A of HRV2, the probably active center can be ascribed to amino acids 100 to 140 (see FIG. 15). To investigate the role of some highly preserved amino acids in this region, in vitro mutagenesis and the deletion of individual amino acids in this region were carried out using an oligonucleotide cassette. In parallel thereto, this method was used to express native protease 2A. Starting from pEx18521, by digestion with Apa I (nucleotide number 3458 of HRV2 cDNA) and HindIII (restriction cutting site originates from the polylinker region of the vector; see Example 1) in accordance with the manufacturer's instructions (Biolabs), a 264 bp long DNA fragment was obtained which was replaced by two double-stranded oligonucleotides with Apa I/HindIII sticky ends. This DNA fragment synthesized from the two double stranded oligonucleotides WT 12 and WT 34, unlike the 264 bp fragment of pEx18521, contains only the 2A specific sequence. Two stop codons in phase were additionally introduced after the codon for the last amino acid (glutamine) of the 2A. As a result, the translation breaks off exactly after the last amino acid of 2A (glutamine) of the 2A. As a result, the translation breaks off exactly after the last amino acid of 2A (glutamine 142)

and after self-cleavage between VP1 and 2A, there is the possibility of a production system for a native protease 2A (see FIG. 17). The purified, double-stranded ApaI/HindIII fragment was sequenced, a positive clone was selected and used for expression studies and transactivity tests. Expression was induced as described in Example 2 and produced the results shown in FIG. 18. When staining is carried out with Coomassie blue (FIG. 18 coomassie blue), using the expression system pEx2A, the 50K cleavage product is recognized, consisting of 98 amino acids of the MS2 polymerase, the C-terminal part of VP3 and the entire VP1. Band D in FIG. 18 Coomassie blue, trace 5, represents the native protease 2A; the band A at about 65K represents the unprocessed form of pEx2A. The Western blot with HRV2 antiserum, carried out as described in Example 2, shows a similar pattern to that obtained when pEx18521 is used (FIG. 18) anti HRV2). If, however, an antiserum is used (PC20; see Example 7) which is directed towards a peptide containing the last 20 amino acids of the protease 2A of HRV2, in the case of pEx2A, a specific band is recognized corresponding to mature 2A (FIG. 18, anti PC20, trace 5, band D). In order to check that this really is the protease 2A of HRV2 and to demonstrate that the in vivo cleavage site (Kowalski et al., supra) had been recognized, band D was eluted from the gel (as described in Examples 1 and 2) and subjected to N-terminal sequencing (Hunkapiller, M. W. et al., Science 219:650–659 (1983)). The sequence was identical to the amino acids shown at the N-terminus of 2A in FIG. 15. Surprisingly, when anti-PC20 antiserum was used, the cleavage product of pEx198251 (2A+N-terminal parts of 2B) was not recognized by this antiserum. Possibly, the fusion component results in a different conformation of the protein which cannot be recognized by the peptide antibody or the Pc20 antibody may react only with the free C-terminus of 2A.

Using the oligonucleotide cassette described above, mutations or deletions were introduced into the probably active center of 2A by exchange with other oligonucleotides (see FIGS. 15 and 17). These mutants were cloned, sequenced and expressed as described for pEx2A. FIG. 18 also shows Coomassie blue and Western blots with HRV2 and PC20 antiserum of these expression products. None of the mutants, apart from pEx2A[Pro 103—Gly] showed any further proteolytic activity The mutations Pro 103— Gly results in a reduction in the proteolytic activity to about 70% (see FIG. 18 Coomassie blue and 18 anti HRV2).

Although a cysteine is obviously functioning as a nucleophile, the homology of the region around the probably active center to the serine proteases (such as chymotrypsin) is surprisingly greater than that with the cysteine proteinases (see FIG. 20). The comparisons were obtained with the protein sequence data banks PIR (Sidman, K. S. et al., Nucleic Acids Res. 16:1869–1871 (1988)) and SWISSPROT (Cameron, G. N. Nucleic Acids Res. 16:1865–1287/67 (1988)) using the FASTP program (Lipman, D. J. et al., Science 227:1435–1451 (1985)). When the probably active center of the protease 2A was compared (see FIG. 15), homologies were surprisingly found only with serine proteases but not with cysteine proteases. Similar results were obtained in 1986 by Gorbalenya et al. (Gorbalenya, A. E. et al., FEBS 194:153–257 (1986)) for the protease 3C of polio virus, although substantially lower homology was found. It is noticeable that the cysteine 6 amino acids after the probably active nucleophile is conserved in the serine proteases and all the 2A proteases but not in the 3C proteases.

In the case of the protease 2A it seems as if a cysteine is functioning as a nucleophile in the conserved environment (GDSGG) of the serine proteases (FIG. 20). From the mechanistic point of view, the 2A proteases, therefore, surprisingly belong to the category of cysteine proteases, although the environment is typical of that of serine proteases. Certain other groups are also well conserved, e.g., the glycine and the cysteine in front of the active center and the glycine in front of a hydrophobic amino acid after the probably catalytic center (see FIG. 15). Since the homology with cysteine proteases is very slight, as described above, it is also doubtful whether the conserved histidine (His114 in HRV2A) can be regarded as a functional analogue to the histidine of the cysteine proteases (e.g., papain). The mutation of the histidine 114 in HRV2did show that it is essential for the activity but did not show whether it is directly involved in the catalytic mechanism. Moreover, a conserved aspartic acid and a second conserved histidine are found in all the 2A and 3C proteases investigated hitherto. This might be an indication of the possible existence of a "charge relay system", similar to that in chymotrypsin. The fact that the proteolytic activity disappears in both cases when the two cysteines of pEx2A (106 and 112) are replaced apparently conflicts with the results in Example 4. However, it should be borne in mind that the mutation in pEx18521 concerns an expression product which unlike pEx2A has an additional C-terminal fusion protein component of 39 amino acids from 2B plus 22 amino acids (from the vector), which may exert considerable influence on the stability and hence on the activity of 2A (e.g., the linking of another disulphide bridging bond).

Furthermore, as described in Example 8, cysteines were replaced by serines (taking up approximately the same space), whereas in Example 4 cysteines were replaced by tryptophan groups (taking up considerably more space) which may lead to structural changes.

In order to investigate the transactivity in vitro, a 16 amino acid long peptide was used as the peptide substrate (ac-TRPIITTAGPSDMYVY). It contains 8 amino acids before the 8 amino acids after the expected cleavage site of 2A (the cleaving occurs between the amino acids underlined). The original peptide substrate 16 amino acids long and a reference peptide which represents the C-terminal cleavage product (GPSDMYVY) were separated on an HPLC column. Expression of the 2A expression systems was induced in the E. coli strain 537 as described in Example 2. After any insoluble matter had been removed, the supernatant was mixed with an aqueous peptide solution of Ac-TRPIITTAGPSDMYVH and incubated. After working up, the peptide-containing supernatant was separated by chromatography. FIG. 19 shows the HPLC profiles of the peptides after incubation of th peptide substrate in various bacterial extracts. When the extract of E. coli cells possessing the pEx2A expressions system is used, the peak $t_R$=20.8 min disappears (uncleaved peptide substrate; Ac-TRPIITTAGPSDMYVH; open arrow shown in heavy lines; absorbs at 214 nm and at 280 nm). Two new peaks are recognizable; one represents the N-terminal cleavage product (Ac-TRPIITTA; solid vertical arrow; $t_R$=16.8 minutes; absorbs only at 214 nm); the second peak represents the C-terminal cleavage product (GPSDMYVH; solid horizontal arrow; $t_R$=12.1 minutes; absorbs at 214 nm and at 280 nm). The fat that the peak with a retention time of $t_R = 12.2$ minutes actually represents the C-terminal cleavage product was verified on the one hand by comigration of this cleavage peptide with the reference peptide (see FIG. 19, number 2), and also by N-terminal sequencing as described above. The cleavage product with the retention time $t_R = 16.8$ minutes cannot be sequenced because of its blocked N-terminus. Apart from pEx2A, only the expression system pEx2A[Pro 103—Gly] shows any transactivity, albeit drastically reduced (about 10%; see FIG. 19, number 4). None of the other mutants of pEx2A shows any transactivity (FIG. 19). It is particularly surprising and noticeable that even the proteolytically active expression system pEx18521 shows no transactivity. Obviously, the C-terminal fusion component (39 amino) acids of 2B and 22 amino acids of the vector DNA) influences the activity in trans, but not the activity in cis, because of the solubility of the fusion protein of 2A (FIG. 19, number 5).

The present invention provides an expression system with which it is possible to discover potential inhibitors of P2A and optimize them; a basic prerequisite for the conversion of the therapeutic concept which appears to be convincing, namely of suppressing the maturation process of the viral system necessary for viral infection of suppressing the proteolytic activity of the viral protease P2A. Because of the marked homology of the P2A region with other groups of Picornaviridiae, it is also possible to use the inhibitors discovered by this system according to the invention therapeutically against infections by other Picorna viruses.

The present invention provides, for the first time, an effective "trans assay" for the protease 2A. It has been demonstrated that peptides can be used as cleavage site analogues, thus permitting detailed and rapid biochemical characterization of the protease 2A. With the aid of this "trans assay" according to the invention it is thus possible to test substances for their inhibiting effect with regard to the protease 2A activity; thus, it provides broad-based inhibitor screening. With the aid of this assay it is possible to find a specific viral protease 2A inhibitors of viral proteases, preferably for P2A inhibitors, more particularly for HRV2-P2A inhibitors.

The following examples are illustrative, but not limiting, of the present invention.

EXAMPLE 1

Preparation of an Active and Inactive P2A Enzyme Substrate of HRV2 for Expression in *E. coli*

Figure 3:
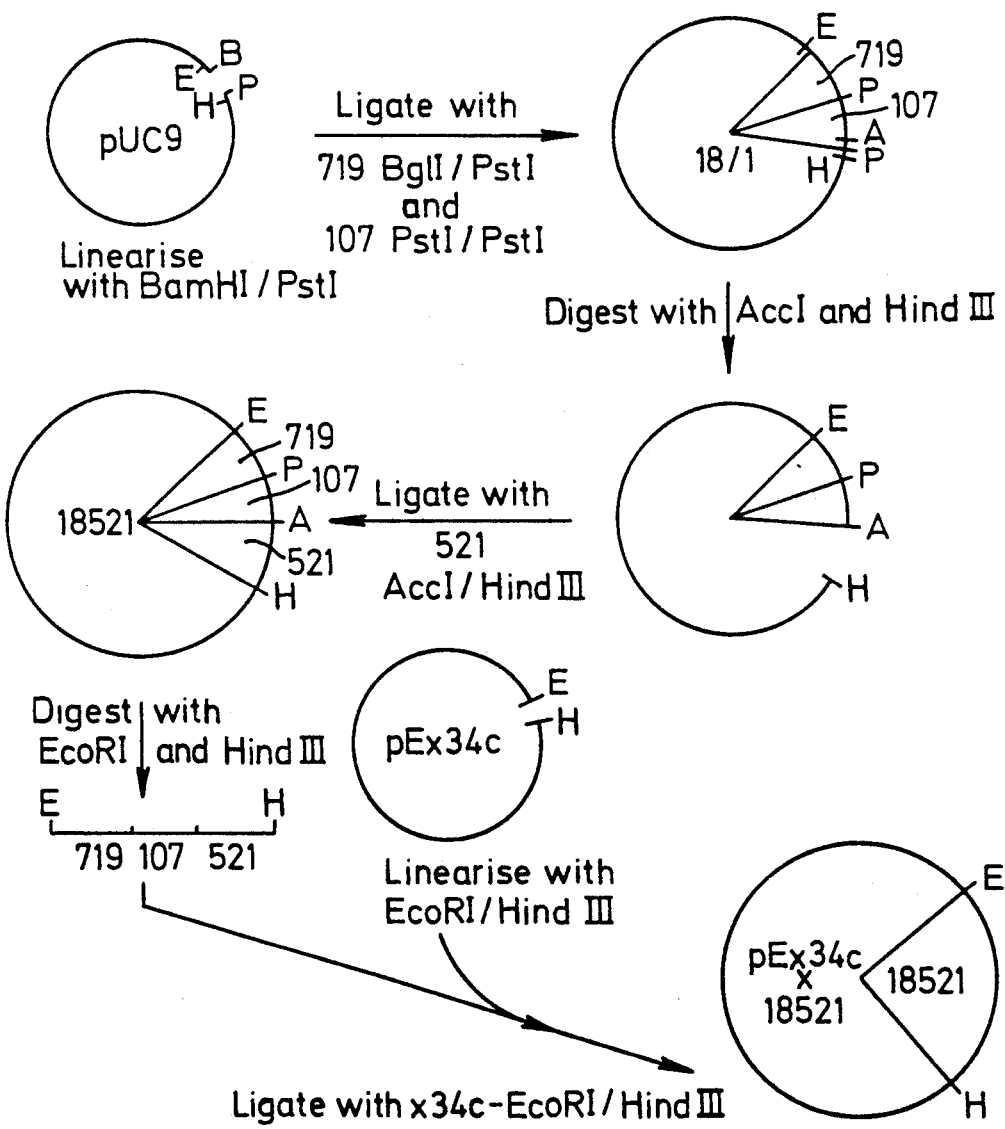
FIG. 3 shows the construction of pEx34c×18521.

Starting from pUC9 and the cDNA clones of HRV2 (FIG. 3) an expression system for P2A was constructed. Initially, about 10 mcg of pUC9 were opened up by double digestion with BamHI and PstI in the polylinker region. The linearized form of pUC9 was separated from traces of the uncut plasmid using Whatman DE812 paper (Dretzen, G. M. et al., *Anal. Biochem.* 112: 295–298 (1981). For this purpose, after resolution of the DNA fragments on agarose gel, a slot was cut in front of and behind the DNA band to be isolated and a strip of DE81 paper was inserted in the slot. Electrophoresis was continued (the gel should not be covered with buffer), until the desired DNA fragment had bound completely to the front strip of DE81. Then, back strip of DE81 paper with the bound DNA fragment was transferred into a 1.5 ml Eppendorf test tube (with an outflow hole in the bottom and polyallomer wool placed above it) and washed twice for 5 minutes with 400 mcl aliquots of washing buffer (0.2M NaCl, 25 mM trisHCl pH=8.0, 1 mM EDTA), the washing solution being caught in the second Eppendorf vessel located underneath by means of brief centrifugation (about 1 second). Then the bound DNA was twice washed off the DE81 paper by 15 minute incubations in 200 mcl of elution buffer (1 M NaCl, 25 mM trisHCl pH-7.5, 1 mM EDTA). The 400 mcl of eluate were centrifuged for 10 minutes in the Eppendorf centrifuge (15,000 g) in order to remove any fragments of paper. The supernatant was carefully transferred into a new Eppendorf vessel, 800 mcl of 96% ethanol were added, precipitation was carried out at −20° C. (for about 2 hours), the precipitate was washed twice with 7% ethanol and dried. In parallel, the plasmid of clone 719 was digested with BglII and PstI and the plasmid of clone 107 was digested with PstI (FIG. 3). These two plasmids are pBR322 vectors and contain HRV2-cDNA fragments which have been inserted via homopolymeric G-C regions in pBR322. The BglII/PstI fragment of clone 719 represents the HRF2-cDNA region from 2145–2421 (see FIG. 3); the PstI/PstI fragment of clone 107 covers the succeeding region 2421–3100. These two fragments were inserted into the BamHI and PstI site of pUC9, the two cutting sites (BglII and BamHI) being destroyed. This construction was designated p18 (see FIG. 3).

In order to obtain cells viable for transformation, a modification of the method of Mandel and Higa was used (Mandel, M. et al., *J. Mol. Biol.* 53:159–162 (1970)). 0.5 ml of an "overnight culture" of *E. coli* strain HB101 was inoculated into 50 ml of LB medium (10 g/l of tryptone, 5 g/l of yeast extract, 10 g/l of NaCl), grown to an OD600 of about 0.4 and then pelleted for 5 minutes at 5k and 4° C. The bacteria were then carefully resuspended in 25 ml of 0.1M $MgCl_2$ (ice cold), placed on ice for 4 hours and centrifuged for 5 minutes at 5k and 4° C. The cells were taken up in 2.5 ml of 1x storage buffer (0.1M $CaCl_2$/glycerol=4/1 v/v), kept on ice for 20 minutes, aliquotized into 100 mcl batches and shockfrozen in liquid nitrogen and stored at −80° C. 5 mcl of the ligation mixture described above were added to 100 mcl of viable cell suspension thawed on ice, the cells were incubated for 1 hour on ice and for 2 minutes at 42° C. and finally placed on ice for 5 minutes. Before the cells were plated out, 900 mcl of LB medium were added, incubation was carried out for 10 minutes at 37° C. and 200 mcl batches of cell suspension were placed on LB agar dishes (1.5% agar in LB medium with 100 mg/l amplicillin) and incubated overnight. Viable JM 101 cells were transformed with the plasmid p18 as described above. Some of the $Amp^4$ clones obtained were subjected to restriction analysis and plasmid-DNA was obtained on a large scale from one of the positive clones (18/1) (T. Maniatis et al., *Molecular Cloning: A Laboratory Manual*; Cold Spring Harbor, 86ff (1986)). The plasmid was then purified over a Sephacryl-S-1000 column (diameter 0.9 cm, length 20 cm). A TE buffer was used as elution buffer. The eluate was divided into approximately 0.5 ml fractions and the individual fractions were measured out at 260 nm (usually the plasmid peak appears between the 9th and 14th fractions). The beginning of the RNA peak can be expected from the 17th fraction onwards (OD more than 3.0). The fractions in question were combined and lyophilized, the plasmid was taken up in 0.5 ml of TE buffer, incubated for 5 minutes at 65° C., extracted with phenol/chloroform and chloroform, precipitated, centrifuged, dried and dissolved in 100 mcl of TE buffer. Approximately 10 mcg of plasmid 18/1 were cut with AccI and HindIII (the ACCI site originates from the HRV2-cDNA and the HindIII site originates from the polylinker region of pUC9). In parallel, the clone 521 was digested with AccI and HindIII. The AccI/HindIII fragment of clone 521 includes the HRV2-cDNA of nucleotide number 3075-3698 (FIG. 3). The AccI/HindIII fragment of 521 was ligated into 18/1 (AccI/HindIII) and with this viable JM 101 was transformed as described above. The colonies obtained were investigated by restriction analysis (EcoRI, PstI, AccI and HindIII) and the plasmid of some clones was sequenced. A clone which had the HRV2 sequence from 2145-3698 and the correct reading frame was designated 18521 and selected for expression. In the construction 18521 the homopolymeric G-C regions which also orginates from the cloning in pBR322 are present at the 5' end of the HindIII site. p18521 was cut with EcoRI and HindIII, the fragment was isolated using DE81 paper and inserted in pEx34c (EcoRI/HindIII) by litigation. pEx34 is a 3.0 kb expression vector (a derivative of pPLc24; Remault, E. et al., Gene 15:81-93 (1981)) which contains the following sections:

the prokaryotic ribosomal binding site part of the coding region for the first 98 N-terminal amino acids of the MS2 polymerase; this fusion component has hydrophobic and basic amino acids and brings about a reduction in the solubility of the fusion protein and increases the stability of the expressed product in the cell.

the fusion protein is under the control of the left lambda promoter a small polylinker region in 3 different reading frames (pExa, b and c) with cutting sites for EcoRI, BamHI, HindIII, PstI, BgIII and XbaI makes it possible to insert suitable DNA fragments in phase behind the fusion protein component the "ori" and ampicillin-resistance region of pBR322. E. coli W6 (lambda) consistitutively expresses the gene for the wild-type lambda repressor and is thus suitable for cultivating the pEx plasmids. E. coli 537, on the other hand, carries the cI 853-lambda repressor mutation (inactive at 42° C.) on another plasmid, which also carries a kanamycin resistance gene (Strebel, K. et al., J. Virol. 57:983-991 (1986)). By insertion of the EcoRI/HindIII fragment of p18521 in pEx34c, it was possible to obtain an expression system which includes the region: (VP3)-VP1-P2A-(P2B) of HRV2 (2145-3698; see FIG. 4). This expression system produces a viral polypeptide acting as substrate, which simultaneously has P2A protease activity.

In order to obtain an inactive enzyme substrate for P2A, the expression vector pEx34c×18421 was cultivated in E. coli WS6 (lambda). As described above, the vector was isolated by the large scale preparation technique from 500 ml of an overnight culture. 2 mcg of pEx34c×18521 were digested with HindIII and purified using DE81, as described above. Then, the linearized vector was digested with Bal31 nuclease as follows: about 1 mcg of the vector linearized with HindIII was incubated with 1U of Bal31 nuclease (Biolabs) in 20 mM of trisHCl pH=8, 600 mM of NaCl, 12 mM of MgCl$_2$ and 1 mM of EDTA. Aliquot samples were taken after 1-2-3-4-5-6 and 8 minutes and digestion was stopped by the addition of EDTA (final concentration 30 mM). The DNA was recovered by ethanol precipitation and 100 ng of the plasmid were incubated with 100 U of T4 ligase in 10 mM of trisHCl pH=7.5, 6 mM MgCl$_2$, 6 mM BME and 1 mM ATP overnight at 15° C. The T4-DNA ligase mixture was used directly for the transformation of E. coli W6 (lambda). Some of the clones were picked and the particular plasmid DNA was sequenced according to the Maxam and Gilbert (Maam, A. et al., Nuckleic Acids Res. 65:499-560 (1980)). A clone whose cDNA ends with the HRV2 nucleotide number 3321 (see Skern, T. el al., Nucleic Acids Res. 13:2111-2126 (1985)) was designated 18731. This deletion mutant of 18521 was used for expression studies as an inactive P2A enzyme substrate.

EXAMPLE 2

Expression and Detection of Fusion Proteins

The plasmids pEx34c×18521 and plasmids of clones of the Bal31 digestion of pEx34 c×18521 were transferred into E. coli cells. The cells were cultivated overnight at 28° C. in LB medium (+100 mg of ampicillin/l and 25 mg of kanamycin/a). The culture were then diluted 1:5 with preheated (42° C.) LB medium without any antibiotics (induction of the lambda-PL promoter) and incubated for 2 hours with vigorous shaking at 42° C. After 2 hours the cells were harvested from 1 ml of the culture (2 min. in the Eppendorf centrifuge 4° C.) and resuspended in 500 ml of cold sonication buffer (150 mM NaCl, 50 mM trisHCl pH=8 and 1 mM EDTA). The cells were broken open by means of an M.S.E. Ultrasonic Power Apparatus (3 times, 5 seconds; 1.7 amp), with a pause of 45 seconds between the individual sonications to prevent the sample from overheating. Any insoluble material was subsequently recovered by 2 minutes centrifuging in the Eppendorf centrifuge and the pellets were dissolved in 200 mcl of sample buffer (4% SDS, 125 mM trisHCl pH=6.8, 10% BME, 10% glycerol and 0.02% bromophenol blue). After heating to 95° C. for 4 min., 10 mcl of the sample were separated on a 10% bromophenol blue). After heating to 95° C. for 4 min., 10 mcl of the sample were separated on a 10% SDS-PAA gel (Lammli, U. K., Nature 227:680-685 (1970)). Control experiments showed that all the expressed proteins are insoluble in sonication buffer. The gels were subsequently stained with Coomassie Brilliant Blue as follows:

Staining: 30-60 min in 50% methanol, 10% acetic acid and 0.1 Coomassie Brilliant Blue Destaining: overnight in 5% methanol and 10% acetic acid Glycerol bath: 30 min in 7% acetic acid and 2% glycerol Ethanol bath: 1 to 2 min in 96% ethanol Drying: on 3 MM paper; 2-3 hours at 80° C. on a gel dryer (Hoefer, SE 1160)

Figure 5:
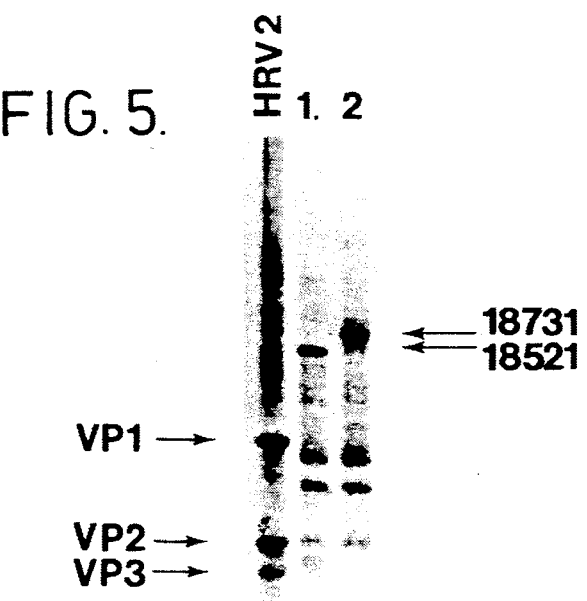
FIG. 5 shows the electrophoretic separation of the expression product of pEx34c×18521 (trace 1) and pEx34c×18731 (trace 2), and the viral coat proteins of HRV2 (trace HRV2) on a 10% SDS polyacrylamide gel and staining with Coomassie brilliant blue.

FIG. 5 shows a typical picture of Coomassie Brilliant Blue staining of an expression of PEx34c×18521 in 537. The deletion mutant 18731 was also separated (see FIG. 5). pEx34c×18731 ends at nucleotide number 3321 and, therefore, no longer possesses the probably active center of P2A (see also FIG. 9). In order to demonstrate the antigenic specificity of these expressed forms of 18521 and 18731, Western blot was carried out using a polyclonal serum against VP1 (VP1 is an integral component of both expression plasmids pEx34c×18521 or 18731). The Western blot was effected as follows: for the electrotransfer of the separated proteins from the gel to the nitrocellulose, 4 layers of 3MM paper (Whatman) and 1 layer of nitrocellulose (Schleicher und Schuell, BA85, 0.45 um) were cut precisely to correspond to the dimensions of the separating gel and preincubated in transfer buffer.

20 mM tris base
150 mM glycine
20% methanol p.a. (pH=8.8; does not need to be triturated).

The transfer sandwich was made up according to the plan below, avoiding air bubbles:

Pol—scotch brite—2 layers 3 MM—gel—nitrocellulose—2 layers 3 MM—scotch brite—+Pole The protein gel was also equilibrated for 2 minutes in transfer buffer before the assembly. The transfer buffer may also be prepared as a 10 ×solution (24.2 g of tris and 112.6 g of glycine per liter without methanol). The transfer was carried out in transfer buffer at about 1 ampere, 2 hours in a protein blot apparatus in the presence of 0.1% Empigen BB (alkyldimethylammonium betaine; No. 62 852, Marchon France S. A.) (R. E. Mandrell et al.; J. Immunol. Meth. 67, page 1 (1984). The efficiency of the transfer was checked using the pre-stained marker proteins.

The filters with the proteins bound thereon were bathed overnight at ambient temperature in 50 ml of blocking solution, namely PBS:

137.0 mM—NaCl
2.7 mM—KCl
8.0 mM—Na$_2$HPO$_4$
1.5 mM—KH$_2$PO$_4$
0.5 mM—MgCl$^2$.6h$_0$
1.0 mM—CaC$^1$.2H$_0$ with 1% BSA, 1% Tween 20 (polyoxyethylene (20) sorbitane monolaurate) and 10% of heat-inactivated fetal calf serum (HIFCS). The polyclonal antiserum against VP1 (ATCC VR-1112 AS/GP) was preincubated before use with an *E. coli* lysate in order to remove *E. coli*-specific antibodies. For this purpose, equal volumes of antiserum and *E. coli* cell lysate were mixed, incubated for 2 hours at ambient temperature, and overnight at 4° C. The cross-reacting *E. coli* proteins were separated from the supernatant as an immunoprecipitate by centrifuging (5 minutes, Eppendorf centrifuge). The nitrocellulose filter was then incubated for 3 hours in blocking solution with the polyclonal antibody (pre-incubated polyclonal antiserum diluted 1/500 to 1/1000 in blocking solution) in a Plexiglass box on a rocker. The filter was then thoroughly rinsed under running tap water (about 15 minutes) and washed three times, for 15 minutes each time, with 50 ml of PBS (+1% Tween 20). In the last step, the filter was incubated for 3 hours at ambient temperature in about 50 ml of blocking solution with the alkaline phosphatase conjugated rabbit anti-antibody (diluted 1/5000 to 1/7500 in "Blocking Solution"). Finally, the filter was again rinsed thoroughly under running tap water (15 min) and washed three times, as described above, with 50 ml of PBS (+1% Tween 20). Staining was carried out in 10 ml of phosphatase buffer:

100 mM trisHCl pH=9.5
100 mM NaCl
5 mM MgCl$_2$ in the presence of the dyes Nitro-blue Tetrazolium (NBT; 165 mcg/ml) and 5-bromo-4-chloro-3-indolyl-phosphate (BCIP; 82.5 mcg/ml). The alkaline phosphatase conjugated anti-rabbit-IgG (Fc) and the dyes NBT and BCIP are obtained from Promega Biotec (Protoblot TM System). The staining reaction was also stopped by rinsing under running tap water after about 1 minute.

FIG. 6 shows a typical picture of a Western blot of pEx34c×18521 or 18731.

EXAMPLE 3

In vitro transcription and translation of pEx34c×18521 and pEx34c×18731.

pEx34c×18521 and 18731 were cultivated, as described above, on a large scale in W6 (lambda) and prepared. 3 mcg of circular plasmids were then used for each batch in the "prokaryotic DNA directed translation kit" made by Amersham (N 380). This bacterial cell-free system permits in vitro expression of genes located on a plasmid, provided that the relevant control signals such as the Pribnow box for initiation of transcription and the Shine-Dalgarno sequence for the translation are present. The expressed products are detected by the incorporation of S-35 methionine. In order to express the two products 18521 and 18731 in vitro, the instructions for incubation provided by the manufacturer were followed. The reference probe used was a pAT153 vector the expression product of which, namely β-lactamase, can be used as a marker on the autoradiogram (FIG. 7, trace 1). Traces 2 and 3 and 4 and 5, respectively show a typical picture of 18521 and 18731, respectively; the high molecular band on the autoradiogram corresponds to the unprocessed 18521 product; the double or triple bands are probably due to breaks caused during transcription or translation. This in vitro system is highly suitable for testing possible inhibitors of P2A.

EXAMPLE 4

In vitro mutagenesis of the catalytic center of P2A

If one looks at the sequence of the P2A region of some Picorna viruses and compares it with the catalytic center of P3C (second virally coded protease), the conservation of the amino acid sequence of this region will be recognised, particularly the probably catalytic center (represented by cysteine and histidine). Both in P2A and in P3C, it must be an SH protease (Cys ... His in the active center), which is proved with comparison of the amino acid sequences in FIG. 8. The HRV2-P2A comprises 142 amino acids, the amino acid residues involved in the catalysis being located in position 114 (histidine) and 106 and 112, respectively, of HRV2-P2A were replaced by phenylalanine by oligonucleotide mutagenesis. The Amersham kit "Oligonucleotide directed by vitro mutagenesis system" was used, which is based on the method of Eckstein et al. (J. W. Taylor, J. Ott and F. Eckstein, 1985, *Nucleic Acids Res.* 43, 8764–8785). First, two mutation oligos were synthesised (Applied Biosystems Model 381A DNA synthesizer, in accordance with the manufacturer's instructions) which is capable of mutagenishing both the cysteine in position 112 which is closer to the histidine (position 114) and the more remote cysteine (position 106) (FIG. 10). In order to obtain single-strand DNA of the P2A region, about 10 mcg of pEx34c×18521 were digested in 100 mcl of 1×Eco/Hind buffer (50 mM NaCl, 75 mM trisHCl PH=7.5, 7.5 mM MgCl$_2$) with 50 U of EcoRI and 50 U of HindIII for 4 hours at 37° C. The EcoRI and 50 U of HindIII for 4 hours at 37° C. The EcoRI/HindIII fragment of 18521 obtained was isolated, as described above, with DE 81 paper from a 1.2% agarose gel and dissolved in 50 mcl of TE buffer. Parallel thereto, 15 mcg of M13mp8 were digested for 2 hours at 37° C. in 30 mcl of lx Eco/Hind buffer with 10 U each of EcoRI and HindIII. Digestion of the restriction enzyme was stopped with 0.5 M EDTA, pH 8 (final concentration 20 mM), extraction was carried out once with phenol/chloroform and once with chloroform, precipitation was carried out with ethanol, then the precipitate was dried and taken up to 5 mcl of TE buffer. 800 ng of EcoRI/HindIII fragment of 18521 and 200 ng of M13mp8 (EcoRI/HindIII) were ligated overnight at 14° C. in 10 mcl of lx ligase buffer (50 mM triusHCl, pH 7.5, 10 mM $MgCl_2$, 10 mM DTT, 1 mM ATP and 50 ng/mcl BSA) with 5 U of T4-DNA ligase. 5 mcl of the ligase mixture were used to transform 200 mcl of viable JM 101; in this and all further steps of the in vitro mutagenesis, the instructions supplied by the manufacturer (Amersham) were followed, with the following modifications: 1) instead of the E. coli strain TG1 recommended by Amersham, JM 101 was used since the insert (18521) in the TG1 cells was not stable in M13mp8 vector; 2) The overnight culture of JM 101 was grown in minimal medium; the minimal medium contains per liter:

10.5 g $K_2HPO_4$
4.5 g $KH_2PO_4$
1.0 g $(NH_4)_2SO_4$
0.5 g sodium citrate$\times 2H_2O$
0.2 g $MgSO_4 \times 7H_2O$
0.01 g thiamine HCl
5.0 g of glucose, the thiamine HCl and glucose only being added after autoclaving of the saline solution in the form of sterile-filtered parent solutions;

3) In order to bring JM 101 cells into the log phase overnight, culture was diluted 1/1,000 in 2x TY medium. The two mutation events for the two cysteines in positions 112 and 106 of HRV2-P2A each resulted in a few hundred white plaques. The mutation efficiency was thus above 95%. Five white plaques were pricked out and transferred into 1.5 ml of 2x TY medium with 20 mcl of JM 101 (overnight culture in minimal medium) and incubated for 6 hours at 37° C. with shaking. Then the culture was centrifuged for 3 minutes (Eppendorf centrifuge) and the double-strand mutated M13mp8$\times$18521 vector was isolated from the cells by the mini preparation method. The isolated M13mp8 plasmids were digested as described above in 1x Eco/HindIII buffer, separated on a 1.2% agarose gel and with the aid of DE81 paper the mutated EcoRI/HindIII fragments of 18521 were isolated. These mutated EcoRI/HindIII fragments were ligated back into the Pex34c vector, and 250 ng of pEx34c (EcoRI/HindIII) and about 200 to 400 ng of mutated EcoRI/HindIII fragment were incubated in 20 mcl of 1x ligase buffer and 1 U T4-DNA ligase (Boehringer Mannheim) for half an hour at ambient temperature and overnight at 16° C. 10 mcl of the ligation mixture were used for transforming viable JM101 cells. Fifteen clones were obtained for pEx34c$\times$18521/106 (corresponding to the plasmid with mutation of the cysteine in position 112). Five clones were selected in each case and their plasmids were isolated on a large scale. The purified plasmids were linearized with HindIII and incubated with 100 U of bacterial alkaline phosphatase in 100 mM trisHCl, pH 8, at 65° C. for 3 hours. After the addition of EDTA to 20 mM, extraction was carried out twice with phenol/chloroform and the DNA was precipitated using ethanol. The DNA was subsequently incubated for 30 minutes at 37° C. in 50 mcl of 50 mM trisHCl, pH 8, 10 mM $MgCl_2$, 5 mM DTE, with 25 mcCi of gamma of P-32 ATP (5,0900 Ci/mmol, Amersham) and 4 U of T4-polynucleotide kinase (BRL) for 30 min at 37° C. and the labeled DNA was precipitated with ethanol. With the aid of EcoRI, which cuts at the 5' end of the insert in pEx34c $\times$ 18521/106 or 112, the insert DNA, which was labeled with P-32 in one strand, was obtained. Sequencing of 18521/106 and 18521/112 was carried out according to Maxam and Gilbert (Maxam, A., et al., Methods Enzymol. 65:499-560 (1980)). One plasmid each of 18521/106 and 112 which contained the corresponding mutated sequence in the catalytic center of P2A was expressed, as described in the second example in the prokaryotic in vitro translation system made by Amersham. The plasmid 18521/112 in which the cysteine in the immediate vicinity of the histidine group has been exchanged for phenylalanine, showed an increased activity of P2A, whereas the mutation of the cysteine which is located further away from the histidine resulted in inhibition of the proteolytic activity (see FIG. 11).

EXAMPLE 5

In vivo labeling of P2A with S-35 methionine

Two different expression plasmids were used for the in vitro labeling of HRV2-P2A. These were the pEx34c$\times$18521 expression system described above and a deletion mutant of 18521, This deletion mutant was prepared as follows: Plasmid DNA of pEx34c$\times$18521 was prepared by the large-scale method (see above). 300 mcg were digested with the restriction enzyme HindIII (Boehringer Mannheim) in a total volume of 200 mcl. 20 mcl batches of this mixture were incubated at 30° C. for 6 to 15 minutes with the exonuclease Bal31 (Biolabs), in accordance with the manufacturer's instructions in a volume of 30 mcl. The nuclease reaction was stopped by the addition of 20 mcl of a 0.25 M EDTA solution and placed on ice. After extraction with phenol/chloroform and chloroform, the DNA was precipitated with ethanol and taken up in 10 mcl of $H_2O$. With the Klenow fragment of the DNA polymerase (Biolabs) and 2.5 mcM of each of the nucleotides dATP, dCTP, dGTP and dTTP, projecting ends of the plasmid DNA were filled in. The plasmids were extracted and precipitated as described above. After further digestion with PstI (Boehringer Mannheim), the fragments were separated on an agarose gel and eluted using DE 81 paper. 10 mcg of the BLUESCRIPT vector (Stratagene Clonging Systems) were digested with EcoRV and PstI, purified by extraction and precipitated. The isolated fragments, which have a blunt end from the Bal31 digestion and polymerase treatment and an overhanging end from the PstI digestion, were ligated into the cut Bluescript vector (FIG. 13). Viable E. coli strain JM109 cells were transformed with the ligase solution. Transformants were selected on agar plates with ampicillin and X-Gal/IPTG. From the time values 7, 9, 11, 13 and 15, 109 deletion mutants were obtained. In order to locate the size and position of the deletions, plasmid DNA was prepared from these clones by the mini preparation method, cut with PstI and HindIII and separated on an agarose gel. The PstI site was maintained by the ligation, whereas the HindIII site originates from the polylinker of the BLUESCRIPT vector and is located only 3 nucleotides after the insert. By size comparison with a marker (lambda DNA digested with HindIII) and with one another, it was possible to identify those clones the deletions of which affect only the C-terminus of P2A. Fifty-four clones were sequenced by the dideoxy method of Snager et al. (Zimmerman et al., *Proc. Natl. Acad. Sci. U.S.A.* 75:4257-4261 (1978)) with an oligonucleotide primer (Applied Biosystems). Twenty-nine clones which had deletions in the region of the catalytic center of the protease P2A and towards the C-terminus of P2A were cloned back into the pEx34c vector. In order to do this, 1 mcg portions of plasmid DNA were cut with PstI and HindIII, separated on an agarose gel, and the smaller fragments were isolated using DE 81 paper (see Example 1). The vector pEx34c×18521 was also digested with these enzymes and the larger fragment was isolated from the gel. After ligation of the deletion fragments with the vector fragment, viable *E. coli* strain 537 were transformed. The expression and detection of fusion proteins was effected by Western blot analysis with a polyclonal serum against VP1. The clone 13A, whose C-terminus of P2A had been shortened by 10 amino acids (deletion mutant ends at nucleotide number 3555), showed no further proteolytic activity, whereas a second deletion mutant 13W, from which six amino acids were missing from the P2A-C terminus (ending with nucleotide number 3569), did show proteolytic activity. This means that the C-terminal region of b 2A can be shortened by at least six amino acids without affecting proteolytic processing. The deletion between the 10th and 6th amino acids of the P2A-C terminus obviously results in the destruction of an essential part of P2A (see FIG. 14).

Another deletion mutant of 18521 which had no proteolytic function of P2A, ends with the region coding for HRV2 18 amino acids before the carboxy terminus of P2A. This mutant was designated 13L (FIG. 14). The two expression plasmids 18521 and 13L in *E. coli* strain 537 were cultivated overnight at 28° C. as described in Example 1. Then, 100 mcl of the cell suspension were diluted in 5 ml of M9 medium:

- 10 ml—10x M9 salts (see Maniatis, T., loc. cit.)
- 0.5 ml—1M MgSO$_4$
- 1 ml—20% glucose
- 0.2 ml—thiamine solution (20 mg/ml)
- 1 ml—Biotin solution (0.2 mg/ml)
- 0.1 m—amino acid solution of Ile, His, Val, Thr and Leu; in each case 20 mg/ml 0.01 ml 1M CaCl$_2$ made up to 100 ml to an OD600 of 0.15 (corresponding to about 100 mcl of cell suspension in 5 ml of M9 medium). The culture was then grown at 28° C. until an OD600 of 0.3 was obtained (about 2 hours at 28° C.). Expression of the HRV2 sequences controlled by the left-hand leader promoter was carried out as described in Example 1 (2 hours at 42° C.). After expression had been induced, 1 ml of the cell suspension were taken, briefly centrifuged (30 seconds in the Eppendorf centrifuge) and taken up in 100 mcl of M9 medium (+100 microCi of S-35 methionine). The cells were briefly incubated (3 minutes at 42° C.) and the reaction was stopped with cold PBS. The cells were briefly centrifuged and resuspended in 1 ml of PBS in order to eliminate excess radioactivity. The samples sonicated as in Example 1 were centrifuged for 3 minutes and the pellet was dissolved in 50 mcl of Lammli sample buffer. The supernatant from the cell lysates was mixed with 200 mcl of 50% TCA, incubated for 30 minutes at 4° C., centrifuged for 10 minutes and the pellet was dissolved in 50 mcl of Lammli sample buffer. 10 mcl passages of the example were separated on a 12.5% SDS-PAA (thickness 0.75 mm). FIG. 12 shows the autoradiogram of this experiment. Both the supernatant and the pellet of the expression system of 18521 show a specific band which represents P2A (plus part of P2B). This band cannot be found in the expression system of the deletion mutant 13L (see FIG. 12).

EXAMPLE 6

Identification of an essential amino acid (Arg 134) in the C-terminus of the protease 2A If one looks at the amino acid sequence of 2A and its highly conserved amino acids within the Rhino, Polio and coxsackie viruses (see FIG. 15), it will be found that within the last 6 and 10 amino acids from the C-terminus of 2A only the arginine in position 134 is conserved. In order to discover whether this group has a fundamental importance in catalysis, the arginine 134 was converted by in vitro mutagenesis into a glutamine. The mutagenesis was carried out on a 1.3 kb Pst I/HindIII fragment of pEx18521 (corresponding to PEx34cx18521), which had been subcloned into the PstI/HindIII site of BLUESCRIPT. This in vitro mutagenesis controlled by an oligonucleotide was carried out using an Amersham kit (oligonucleotide-directed in vitro mutagenesis) following the manufacturer's instructions. Three positive clones were sequenced, as described above. The mutated PstI/HindIII fragment was used to replace the Wild-type PstI/HindIII fragment in pEx18521. The mutated expression vector pEx18521 [Arg 135—Gln] was expressed as described in Example 2 and the pattern of the expression products was analyzed on a protein gel and using a Western blot (see FIG. 16). Mutation of the arginine 134 into the glutamine results in the disappearance of the proteolytic activity; the unpossessed 75K protein is formed exclusively.

EXAMPLE 7

Production of the peptide antibody PC20

The last 20 amino acids of the Protease 2A constitute a potential antigenic determinant. One peptide (PC20) which contained precisely this amino acid sequence, was synthesized and described in Example 9 and used to induce antibodies in rabbits: 570 mcg of this peptide were taken up in 0.4 ml of PBS solution and drawn up in a 5 ml syringe. 0.5 ml of Freund's adjuvant (CAF; GIBCO) were drawn up in a second 5 ml syringe and the two components were then mixed together using a three-way stopcock value until an emulsion had formed. The rabbit was punctured through a artery in the ear in order to obtain a pre-serum for the negative control. Immunization was carried out by subcutaneous injection of the peptide/CFA mixture at four different places (0.2 ml per injection site) on its back area. After five weeks, a booster injection of 1.2 ml of peptide solution was administered in a quantity of 0.2 ml by intramuscular route into the back area. Eight days later, blood was taken by cardiac puncture. The blood was allowed to clot at ambient temperature, any fibrin and any shaped matter were removed with a sterile rod, and the blood was centrifuged at 2,000 rpm. Aliquots of the serum were made and stored at −18° C.

Investigation of the hydrophobicity profile of the Protease 2A according to Kyte and Doolittle (Kyte, J., et al., *J. Mol. Biol.* 157:105-132 (1983)), and secondary structural analysis of this region (Pallai, P. V., et al., *J. Am. Chem. Soc.* 85:2149-2154 (1983)) indicated that the last 20 amino acids of the Protease 2A are a potential antigenic determinant. One peptide (PC20) which contained precisely this amino acid sequence was therefore synthesized, for example in accordance with the method of Example 9, and used to induce antibodies in rabbits. A rabbit was punctured in the artery in the ear in order to obtain a pre-serum for the negative control. Immunization was carried out by subcutaneous injection of a peptide/CFA mixture at four different sites in the back area. Aliquots of the serum were made and stored at =18° C.

EXAMPLE 8

Establishment of an expression system for producing native Protease 2A and analysis of point mutants in the probably active center of 2A In order to investigate the role of some highly conserved amino acids in the region of the probably active center (see FIG. 15), in vitro mutagenesis and deletion of some individual amino acids in this region were carried out using an oligonucleotide cassette. Parallel thereto, this method was used to express native Protease 2A. Starting from PEx18521, by digestion with ApaI (nucleotide number 3458 of HRV2 cDNA) and HindIII (restriction cutting site originating from the polylinker region of the vector; see Example I) in accordance with the manufacturer's instructions (Biolabs), a 264bp-long DNA fragment was obtained which was replaced by two double-stranded oligonucleotides WT12 and WT34 with ApaI/HindIII "sticky ends" (see FIG. 17). First, 1 mcg of the single-stranded oligonucleotides WT1, WT2, WT3 and WT4 were kinased in 10 mcl each of (20 mM TrisHCl, pH 7.5, 10 mM MgCl$_2$, 20 mM DTT and 1 mM ATP) with 2 U of T4-polynucleotide kinase (Biolabs for 30 minutes at 37° C. Then the kinase mixtures of WT1 and WT2 were combined, as were WT3 and WT4, then incubated for 10 minutes at 68° C., 30 minutes at 45° C., 10 minutes at ambient temperature and finally briefly on ice. The kinased and hydridized oligonucleotides were then combined, the concentration was adjusted to 1 mM, a 10 mM ATP solution and 28 U T4-DNA ligase (Boehringer Mannheim) were added for the ligation. The ligation itself was carried out initially for two hours at 20° C., then a further 7 U of T4-DNA ligase were added and the ligation mixture was incubated for 40 hours at 14° C. Subequently, the ligation mixture was incubated for 10 minutes at 70° C., adjusted to 100 mM with a 1 M NaCl solution and the resulting multimeric forms of the oligonucleotide were "recut" with 50 U of ApaI and 20 U of HindIII. Purification and isolation of the correct double-stranded Apa/HindIII fragment and the back-cloning of this fragment into pEx18521 (cut with ApaI and HindIII) and identification by sequencing were carried out as described in Example 1. A positive clone was selected and used for expression studies and transactivity tests.

Expression was induced precisely as described in Example 2 and gave the results shown in FIG. 18.

EXAMPLE 9

In vitro transactivity test for the Protease 2A using a cleavage site peptide

The peptides used in this Example were synthesized by the "solid phase" method (Merrified, R. B., *J. Am. Chem. Soc.* 85:2149–2154 (1963) purified by reverse phase HPLC (0.1% trifluoroacetic acid and acetonitrile as the mobile phase) and identified with the aid of HPLC analysis, fast atom bombardment mass spectrometry (FAB-MS) and amino acid sequencing (Hunkapiller, M. W., et al., loc. cit.).

As described in Example 2, the expression of the 2A expression systems was induced (see Example 8) in *E. coli* strain 537. After two hours incubation at 42° C., the cells from 1 ml of the culture were harvested (2 minute Eppendorf centrifuge, 4° C.) and resuspended in 500 mcl of HEPES buffer (100 mM NaCl, 10 mM HEPES, pH 7.4, 1 mM EDTA and 1 mM DTT). The cells were broken up using an M.S.E. ultrasonic power device (3×30 seconds; in a bath of icewater), whereas a pause of 30 seconds was included between the individual sonications to prevent the samples from overheating. Insoluble material was removed by centrifuging (2 minute Eppendorf centrifuge) and 100 mcl of the supernatant were mixed with 5 mcl of an aqueous peptide solution of Ac-TRPIITTAGPSDMYVH (4 mg/ml) and incubated for 20 minutes at 27° C. The reaction was stopped by adding the same soluble of 1 M HClO$_4$. The samples were then incubated on ice for 20 minutes, centrifuged for 10 minutes at 4° C. (Eppendorf centrifuge), an equal volume of 1.4 MN K$_2$HPO$_4$ was added, the mixture was incubated for five minutes at ambient temperature and the precipitate formed was removed by centrifuging (5 minute, Eppendorf centrifuge). The supernatant containing peptide was then separated by reverse phase HPLC, using a 0.1% trifluoroacetic acid and acetonitrile as the mobile phase.

The original peptide substrate 16 amino acids long and a reference peptide which represents the C-terminal cleavage product (GPSDMYVH) were also separated on the HPLC column and N-terminally sequenced as described above. FIG. 19 shows the HPLC profiles of the peptides after incubation of the peptide substrate in various bacterial extracts.

We claim:

1. A peptide consisting of TRPIITTAGPSDMYVH, wherein the peptide is capable of being cleaved by P2A of HRV II.

* * * * *